US008524193B2

(12) United States Patent
Madar et al.

(10) Patent No.: US 8,524,193 B2
(45) Date of Patent: *Sep. 3, 2013

(54) NON-INVASIVE DIAGNOSTIC IMAGING TECHNOLOGY FOR MITOCHONDRIA USING RADIOLABELED LIPOPHILIC SALTS

(75) Inventors: Igal Madar, Baltimore, MD (US); Hayden T. Ravert, Bel Air, MD (US); Robert Francis Dannals, Sparks, MD (US); Ursula A. Scheffel, Baltimore, MD (US); James J. Frost, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 1881 days.

This patent is subject to a terminal disclaimer.

(21) Appl. No.: 10/503,690

(22) PCT Filed: Feb. 6, 2003

(86) PCT No.: PCT/US03/03740
§ 371 (c)(1),
(2), (4) Date: Apr. 7, 2005

(87) PCT Pub. No.: WO03/065882
PCT Pub. Date: Aug. 14, 2003

(65) Prior Publication Data
US 2005/0182027 A1    Aug. 18, 2005

Related U.S. Application Data

(60) Provisional application No. 60/354,563, filed on Feb. 6, 2002.

(51) Int. Cl.
*A61K 51/00* (2006.01)
*A61M 36/14* (2006.01)

(52) U.S. Cl.
USPC ....... 424/1.89; 424/1.11; 424/1.65; 424/1.81; 424/1.85

(58) Field of Classification Search
USPC .................... 424/1.11, 1.65, 1.81, 1.85, 1.89, 424/9.1, 9.3, 9.4, 9.5, 9.6, 9.7, 9.8; 568/8, 568/16, 17
See application file for complete search history.

(56) References Cited

U.S. PATENT DOCUMENTS

| 4,446,123 | A | 5/1984 | Woo | |
|---|---|---|---|---|
| 6,190,637 | B1 | 2/2001 | Ino et al. | |
| 6,358,489 | B1 | 3/2002 | Griffiths | |
| 6,555,279 | B2 | 4/2003 | Nakata et al. | |
| 7,112,318 | B2 * | 9/2006 | Madar et al. | 424/1.89 |
| 2002/0061279 | A1 | 5/2002 | DeGrado et al. | |
| 2004/0092825 | A1 | 5/2004 | Madar et al. | |

OTHER PUBLICATIONS

Golub et al., Science, Oct. 15, 1999, pp. 531-537.*
Srivastava et al (Journal of Labeled Compounds and Radiopharmaceuticals, 1990, vol. XXVIII, No. 10, pp. 1161-1169).*
Walker et al (Journal of Thoracic and Cardiovascular Surgery, 1999, vol. 118, pp. 375-382).*
P.C. Srivastava et al., "[(E)-1-[123I]Iodo-1-penten-5-yl]triphenylphosphonium Iodide: Convenient Preparation of a Potentially Useful Myocardial Perfusion Agent." J. Med. Chem., 1984, 27, pp. 978-981.
H. Fukuda et al., "Use of 11 C-triphenylmethylphosphonium for the evaluation of membrane potential in the heart by positron-emission tomography." European Journal of Nuclear Medicine, 1986, 11: pp. 478-483.
B.J.Krause, "Myocardial Perfusion with [11C]Methyl Triphenyl Phosphonium: Measurements of the Extraction Fraction and Myocardial Uptake." The Journal of Nuclear Biology and Medicine, vol. 38, No. 3, 1994, pp. 521-526.
I. Madar, et al., "Enhanced Uptake of [11C]TPMP in Canine Brain Tumor: A PET Study." The Journal of Nuclear Medicine, vol. 40, No. 7, 1999, pp. 1180-1185.
I. Madar, et al., "Preferential Accumulation of 3H-Tetraphenylphosphonium in Non-Small Cell Lung Carcinoma in Mice: Comparison with 99mTc-MIBI." The Journal of Nuclear Medicine, vol. 43, No. 2, 2002, pp. 234-238.
Madar I., et al. Enhanced Uptake of [11C]TPMP in Canine Brain Tumor: A PET Study. J Nucl Med. Jul. 1999;40 (7):1180-5.
Davis R.J., et al. The effect of insulin on plasma-membrane and mitochondrial-membrane potentials in isolated fat-cells. Biochem J. Apr. 15, 1981;196(1):133-47.
Davis R.J., et al. The effect of beta-adrenergic agonists on the membrane potential of fat-cell mitochondria in situ. Biochem J. Sep. 15, 1982;206(3):611-8.
Hockings P. D., et al. The measurement of transmembrane electrical potential with lipophilic cations. Biochim Biophys Acta. Jun. 13, 1996;1282(1):101-6.

* cited by examiner

*Primary Examiner* — D L Jones
(74) *Attorney, Agent, or Firm* — Edwards Wildman Palmer LLP; Peter F. Corless

(57) ABSTRACT

The invention provides lipophilic salts, particularly, lipophilic salts comprising a pharmaceutically acceptable anion and at least one phosphonium or ammonium cation. In certain embodiments, the cation is labeled with one or more radioisotopes. The lipophilic salts of the invention exhibit an affinity for dysfunctional mitochondria, and are useful for the imaging of cardiovascular diseases and disorders. The invention also provides pharmaceutical compositions and methods of using the lipophilic salts.

13 Claims, 13 Drawing Sheets

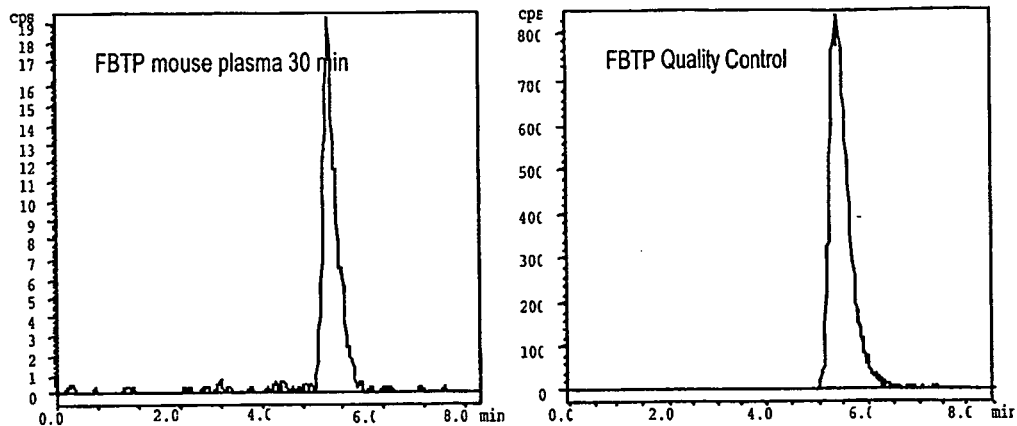
Figure 1  Radiochromatograms of $^{18}$F-FBnTP (quality control) and plasma 30 min p.i. of the tracer into mice.
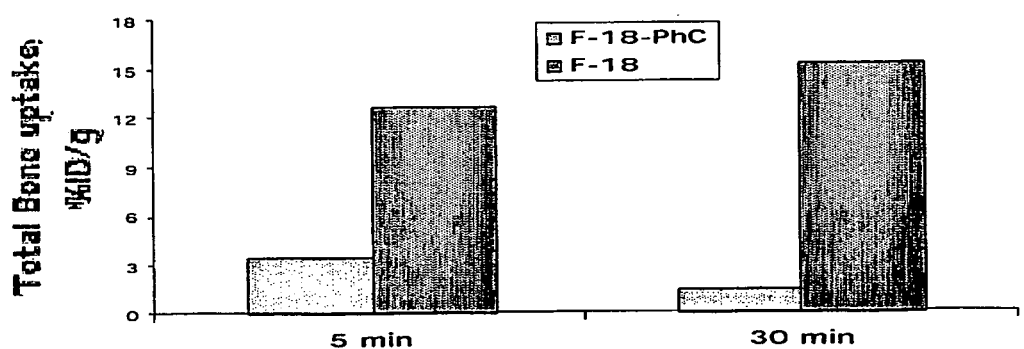
Figure 2: Bone uptake of F-18-FBnTP and F-18 in mice

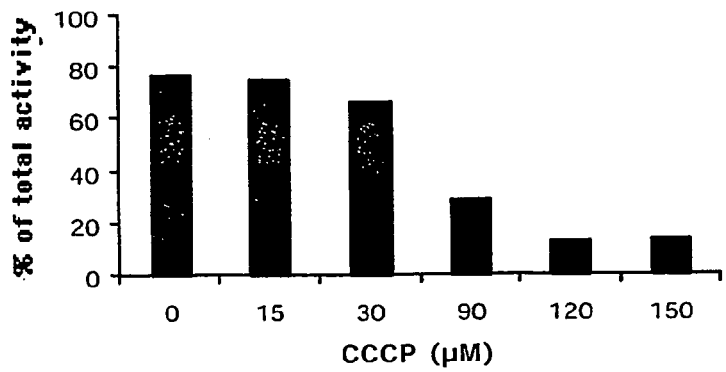
Figure 3. Mitochondrial membrane potential-dependent uptake of 18F-FBnTP in vitro
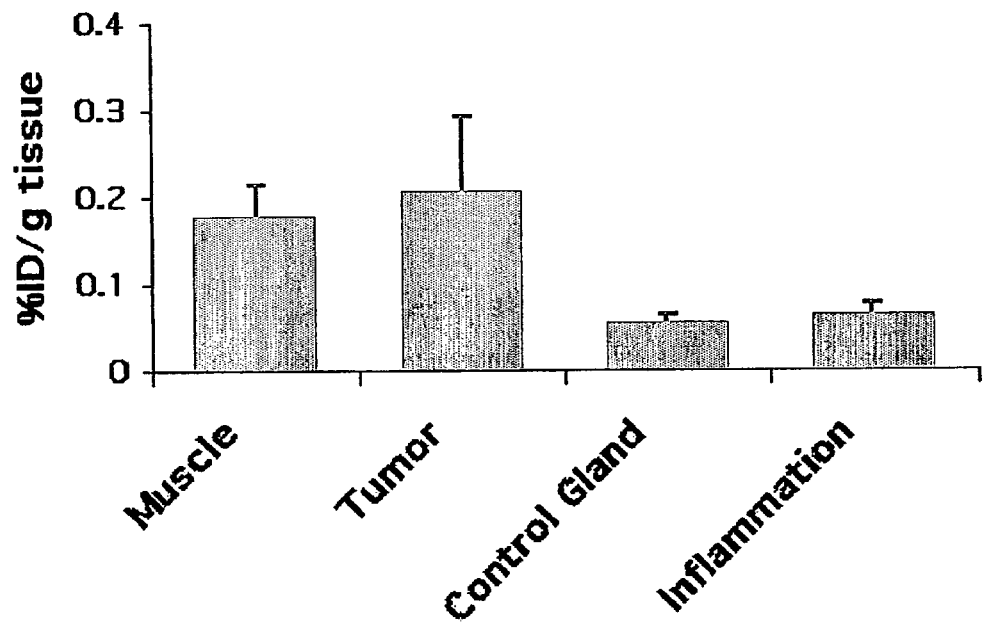
Figure 4. Accumulation of $^{18}$F-FBnTP in malignant (Tumor) and healthy (control) mammary gland and in healthy (Muscle) and inflammation muscle, in rats.

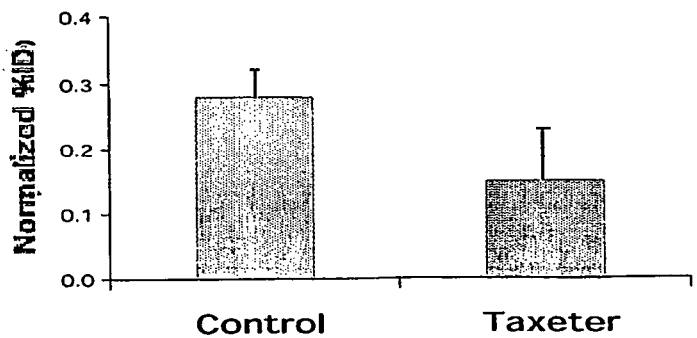
Figure 5: Cellular uptake of F-18-FBnTP in lung carcinoma A549 tumor.
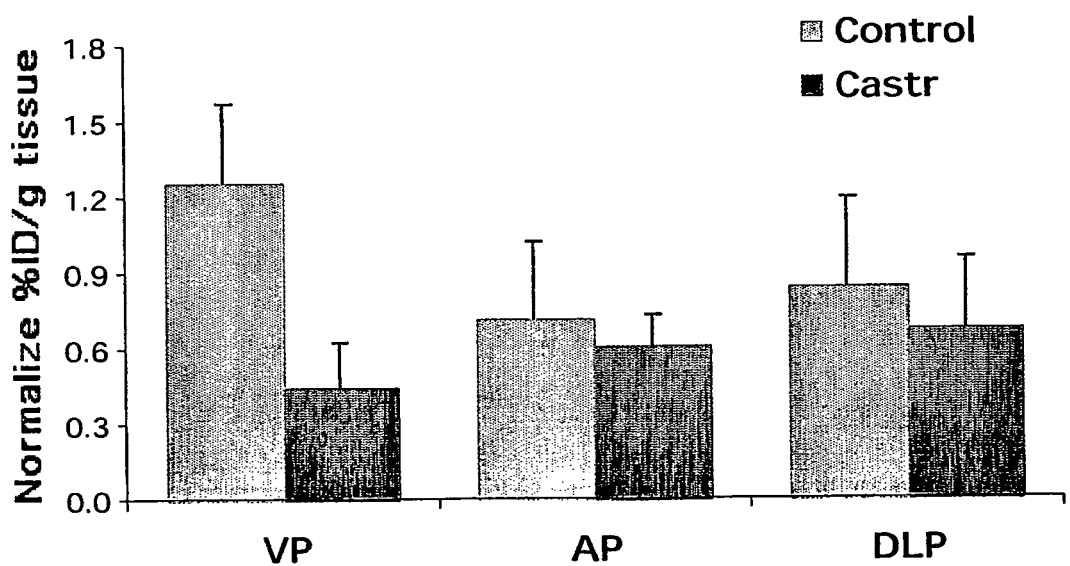
Figure 6: Accumulation of F-18-FBnTP in the prostate lobes 4 days after castration. Castration-produced apoptosis induced significant lobe-specific decrease in the ventral aspect, compared to control

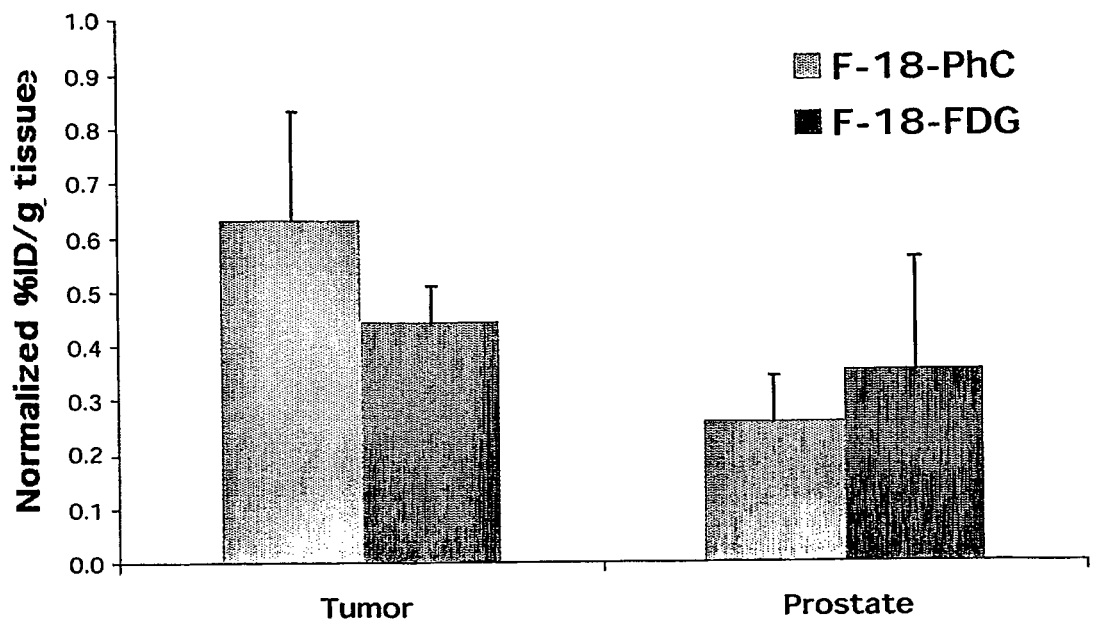
Figure 9: Accumulation of F-18FbnTP and F-18-FDG in prostate tumor in mice.
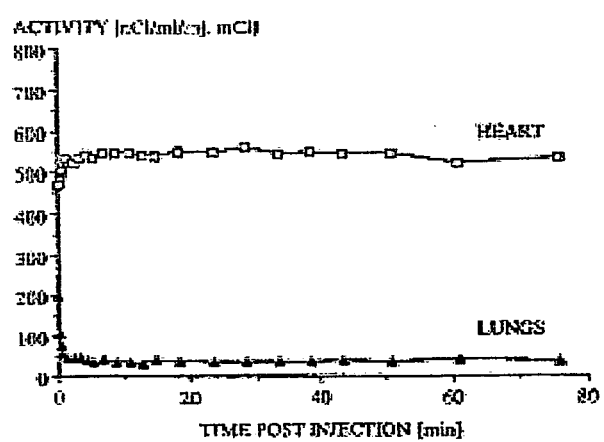
Figure 10: C-11TPMP myocardial uptake

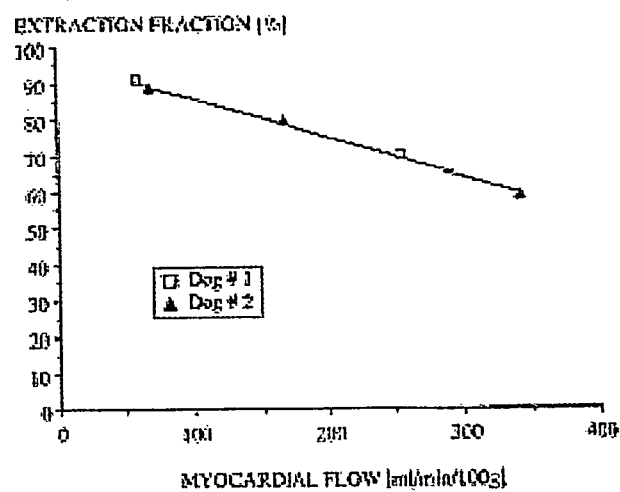
Figure 11: C-11-TPMP extraction fraction
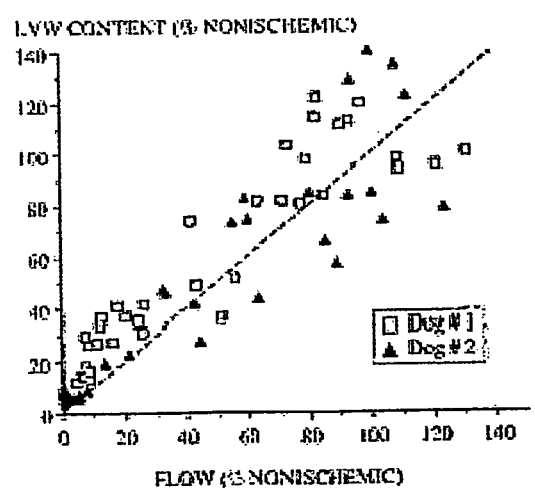
Figure 12: C-11-TPMP myocardial uptake as function of coronary blood flow

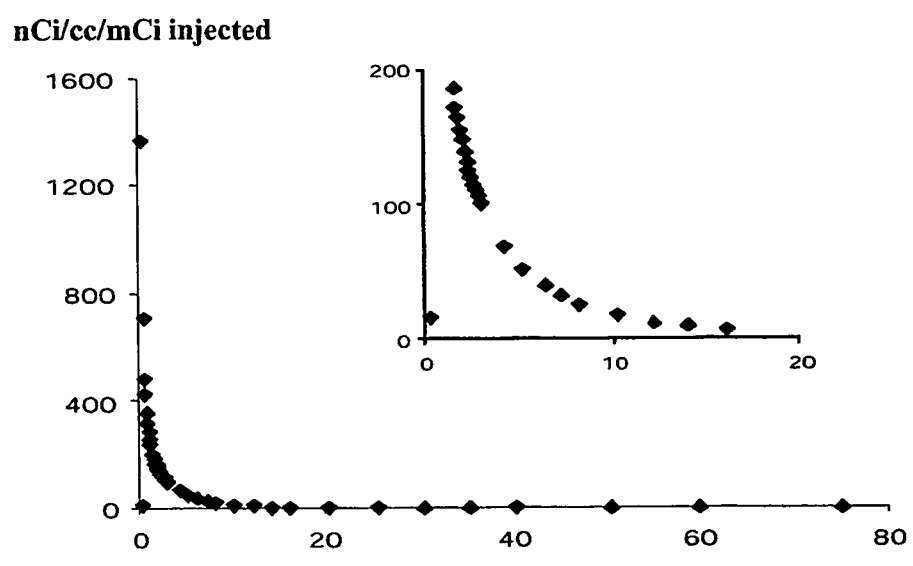
Figure 13: F-18-FBnTP rapid clearance from blood

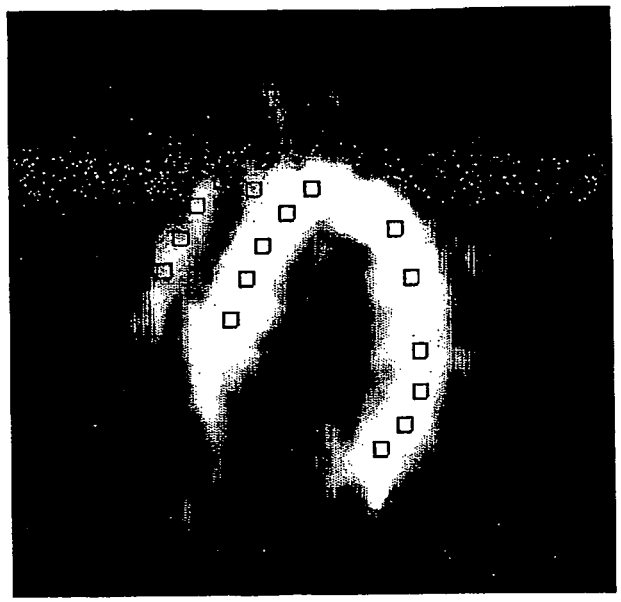
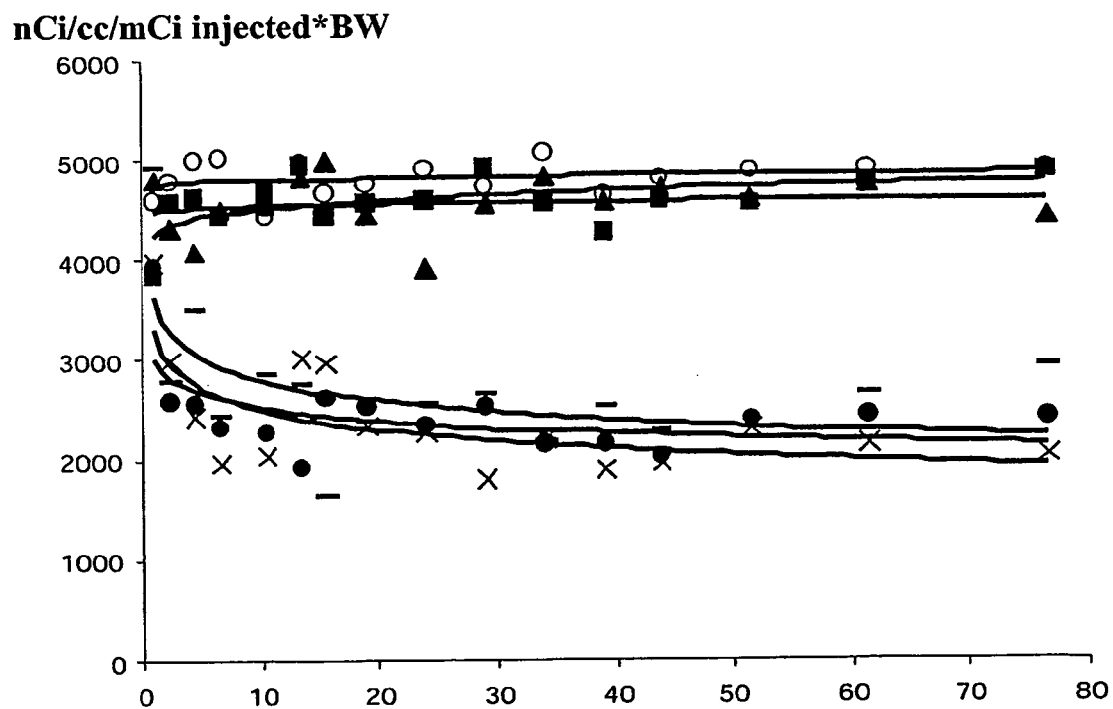
Figure 14: F-18-FBnTP accumulation kinetics in the left and right ventricles in 3 consecutive axial slices (8 to 10). Each trace is the mean of ROIs as above demonstrated. This figure is a good example for the rapid fact kinetics of FBnTP and uniform distribution in the myocardium.

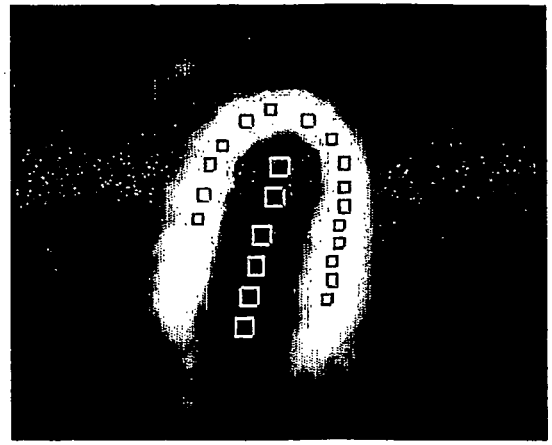
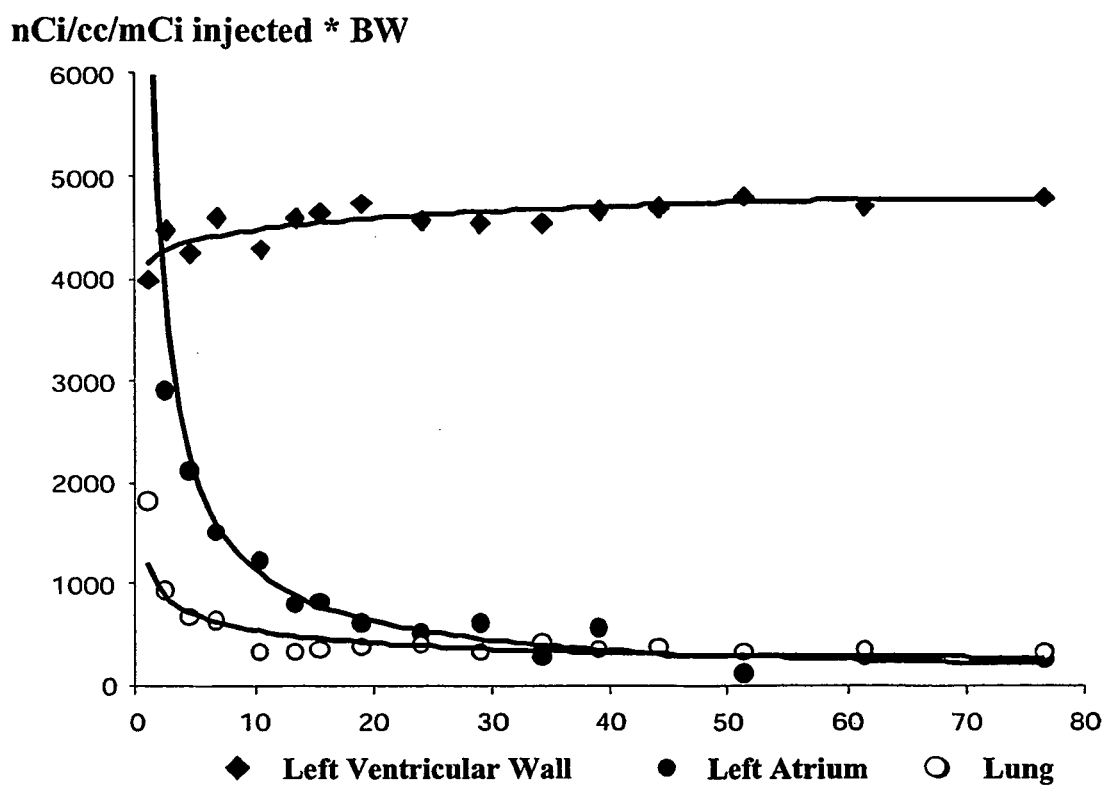

Figure 15: F-18-FBnTP uptake kinetics in the left ventricle and lung. ROIs for generating the left ventricle time-activity curve are presented on the corresponding slice. This figure is an excellent example of the preferential accumulation of FBnTP in the myocardium, compared to the adjacent lungs, resulting in the very high-quality images of the myocardium as presented in the figure below.

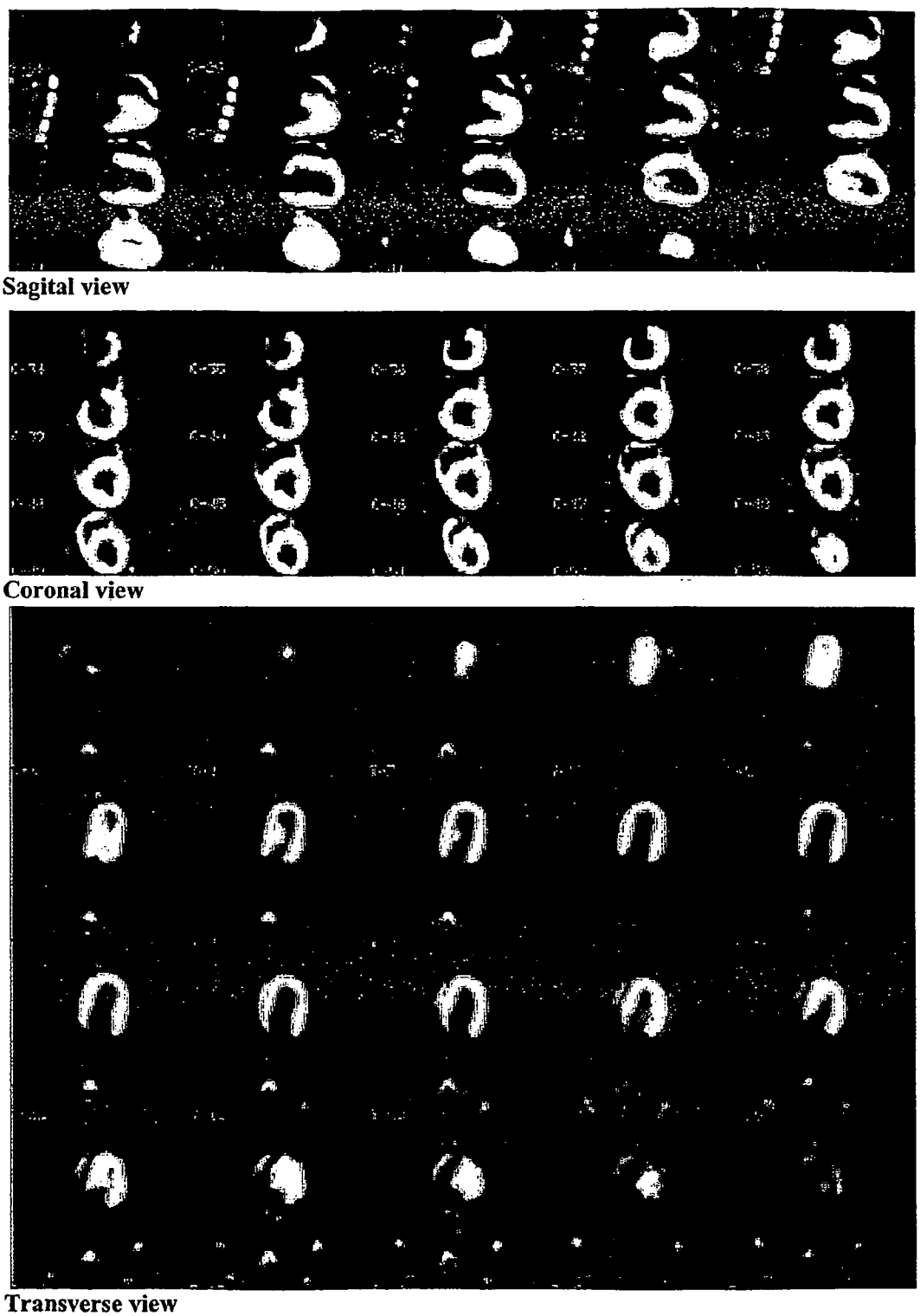
Figure 16: F-18-FBnTP myocardial accumulation in heart failure.

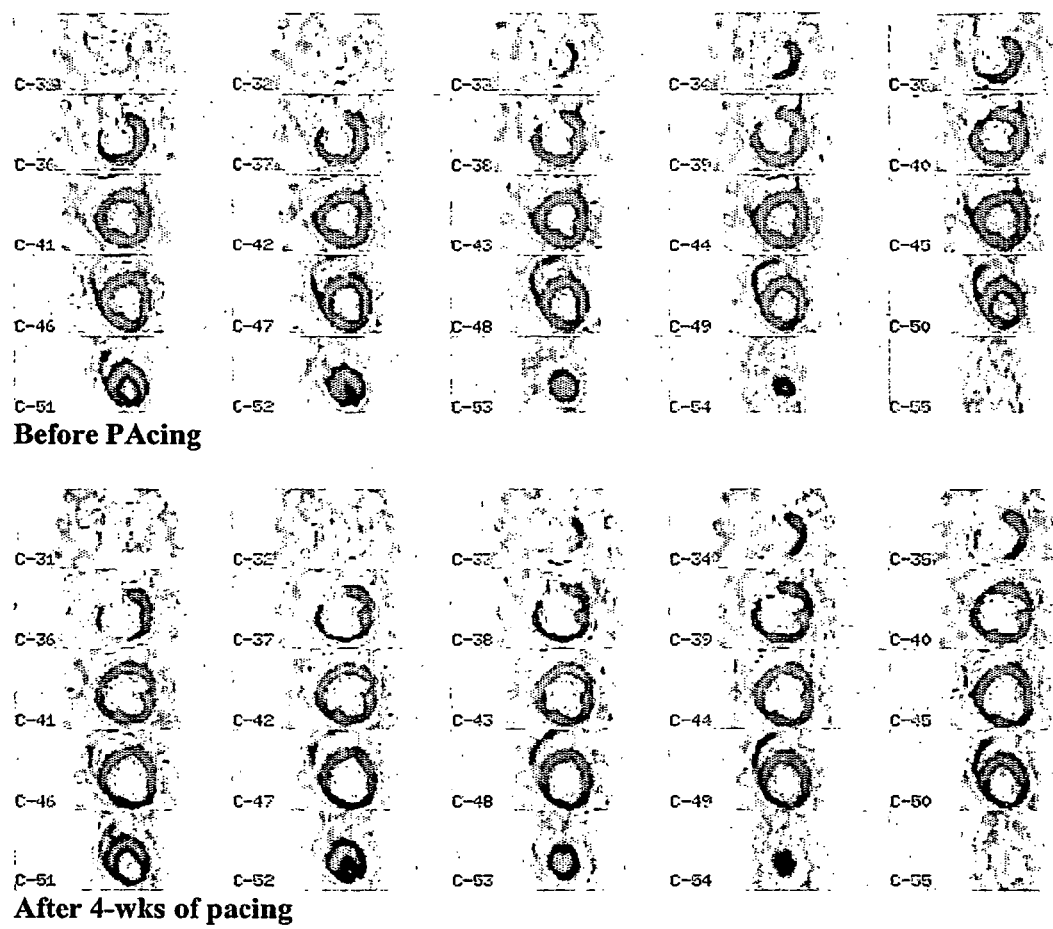
Figure 17: F-18-FBnTP PET short-axis images of the myocardium before and after pacing

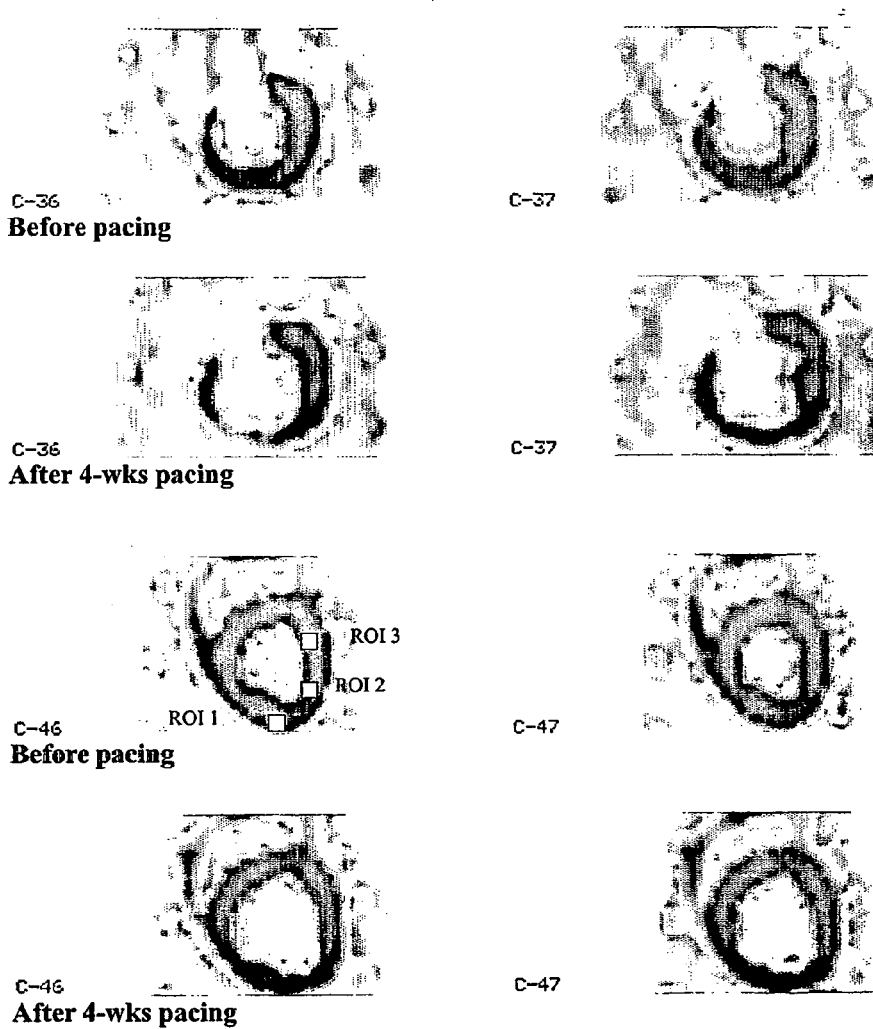
Figure 18: A decrease in F-18-FBnTp uptake in the inferior wall following pacing-induced heart failure.

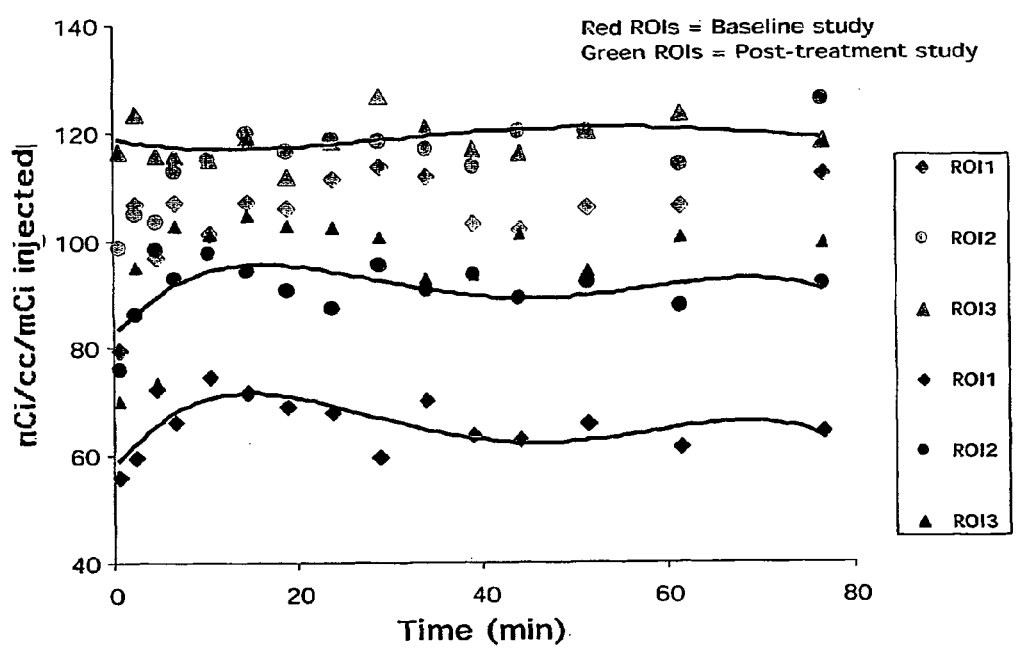
Figure 19: Time-activity course of [$^{18}$F]FBnTP myocardial uptake before (red) and after 4 weeks of pacing. Each data point represents the mean activity of four slices (slice 46 to 49). Positioning of region of interest (ROI) is shown in the left upper cardiac image. The same ROIs template was used to retrieve data in all cardiac sections.

NON-INVASIVE DIAGNOSTIC IMAGING TECHNOLOGY FOR MITOCHONDRIA USING RADIOLABELED LIPOPHILIC SALTS

This application claims the benefit of U.S. Provisional Application Ser. No. 60/354,563 filed Feb. 6, 2002, the teachings of which are incorporated herein by reference.

This invention was supported by National Institute of Health (NIH) Grant No. CA92871. The United States government has certain rights to the invention.

BACKGROUND OF THE INVENTION

1. Field of the Invention

The present invention provides novel radiolabeled lipophilic salts, particularly radiolabeled lipophilic phosphonium and ammonium salts, which are capable of measuring mitochondrial surface potential ($\Delta\Psi m$). This invention also provides pharmaceutical compositions comprising such radiolabeled lipophilic salts. Additionally this invention provides imaging methods for identifying tissues or cells having aberrant levels of mitochondrial activity by selectively localizing radiolabeled lipophilic salts of the invention into dysfunctional mitochondria. The invention also provides on-invasive methods for an early and sensitive detection of tumor response to chemotherapy agents. The invention further provides treatment methods comprising administration of a high energy radiolabeled lipophilic salts to a patient, particularly patients suffering from diseases or disorders associated with mitochondrial dysfunction.

2. Background

Measurement of the mitochondrial membrane potential ($\Delta\Psi m$) provides the single most comprehensive reflection of mitochondrial bio-energetic function primarily because it directly depends on the proper integration of diverse metabolic pathways that converge at the mitochondria. Numerous diseases are associated with mitochondria dysfunction, including cancer, cardiovascular and liver diseases, degenerative and autoimmune disorders as well as aging and new pathologies related to mitochondria are identified each year.

Alterations in $\Delta\Psi m$ is an important characteristic of a vast array of pathologies that either involve suppressed (e.g., cancer) or enhanced apoptosis (e.g., HIV, degenerative disease) as well as >100 diseases directly caused by mitochondrial dysfunction such as DNA mutations and oxidative stress (e.g., various types of myopaties).

There are SPECT imaging probes labeled with a technetium center which are capable of accumulation in the mitochondria and the technetium labeled probes have been used for mitochondria based imaging techniques. There are a number of commercially available imaging probes that detect a given pathology using imaging agents such as [$^{99m}$Tc]MIBI, FDG.

[$^{18}$F]FDG detects malignant lesion due to enhanced glucose metabolism. Further, as mentioned above, [$^{18}$F]FDG is not able to differentiate neoplasm from inflammation. [$^{18}$F]FDG is most effective imaging probe for tumor detection but poorly distinguishes neoplasm from inflammation, posing a frequent diagnostic challenge. In certain organs inflammation (e.g., tuberculosis) is a frequent pathologies among patients with suspected malignant lesion. For example, >10% of pulmonary hot spots indicated by [$^{18}$F]FDG PET are inflammatory process rather than neoplasm, as proven by surgery. In other words, about 10% of lung patients with [$^{18}$F]FDG PET indications may undergo unnecessary chest surgery, for a disease (inflammation) that otherwise can be treated in non-surgical and less costly and morbid approaches.

Current approaches for evaluation of efficacy of chemotherapy relies on alterations in tumor growth rate, a costly approach of limited sensitivity which involves months of follow up, repeated visits in clinic, multiple radiographic scans and frequently a number of treatment cycles.

Technetium labeled mitochondria imaging agents are hampered by several limitations. More particularly, labeling a molecule with $^{99m}$Tc requires a conjugating moiety to complex the technetium ion such that Tc-based imaging agents have a high molecular weight which reduces the permeability of the imaging agent in target areas. Further, technetium imaging agents are imaged with SPECT which has relatively low spatial resolution and sensitivity when compared to comparable PET images.

There are technetium complexes, derivatives of [$^{99m}$Tc] annexin V, for apoptosis imaging by using SPECT. The novelty of the proposed [$^{18}$F]phosphonium cations (PhCs) is that they detect the apoptotic process via a change in $\Delta\Psi m$, whereas annexin V derivatives do so due to overexpression of specific membrane proteins.

[$^{99m}$Tc]annexin V detects apoptosis due to externalization of phosphatidylserine on the outer cytoplasm membrane. This event occurs at the end of the apoptosis process when the fragmented cell is transformed into clusters of molecules (apoptotic bodies). Shortly after the externalization of phosphatidylserine (termed "eat me" phospholipids) the apoptotic bodies are phagocytized by neighboring cells. Therefore, detection of overexpression of phosphatidylserine is limited to a narrow time window which may last a few days only. Furthermore, the time of appearance and the duration of this window may vary among different chemotherapy agents and subjects.

The collapse of $\Delta\Psi m$ is the point of no return of the apoptotic process. Therefore, the collapse of $\Delta\Psi m$ affords the earliest time point to detect apoptosis, rather the last event as in the case of annexin V, and the collapse persists independent of time.

Current approached for the evaluation of myocardial perfusion and viability have several limitations, including masking of myocardial activity by high accumulation in the organs adjacent to the heart (Th-201, [$^{99m}$Tc]MIBI) and short half-life of the isotope ([$^{13}$N]-ammonia and $^{82}$Rubidum), thus limited to PET centers with an on-site cyclotron.

It would be desirable to have a family of lipophilic salts which have an affinity for mitochondria, particularly mitochondria undergoing aberrant activity.

SUMMARY OF THE INVENTION

In view of the high incidence of cancer cases (~1.3 million per year in the USA), the high frequency of chemotherapy applications and the low frequency of successful chemotherapy, there is an urgent need for a non-invasive imaging probe of rapid and sensitive assessment of tumor response to treatment. The need for diagnostic means in oncology is best exemplified by the rapid transition of [$^{18}$F]FDG PET from an investigational to a preferred diagnostic tool for tumor detection within a few years.

There also exists a great need to diagnose and image cardiovascular diseases and disorders, many of which are associates with mitochondrial dysfunction. Thus there is also an urgent need for non-invasive imaging probes for rapid and sensitive measurement of cardiac uptake of imaging agents having an affinity for dysfunctional mitochondria for the imaging of cardiovascular diseases such as myocardial perfusion.

The invention provides novel lipophilic salts, particularly lipophilic salts comprising a pharmaceutically acceptable anion and at least one phosphonium or ammonium cations according to Formula I, and pharmaceutical compositions comprising cations of Formula I and at least one pharmaceutically acceptable carrier or excipient. Preferred lipophilic salts of the invention exhibit high affinity mitochondria, particularly dysfunctional mitochondria with enhanced or suppressed activity.

The present invention provides salts comprising at least one pharmaceutically acceptable anion and at least one cation according to Formula I

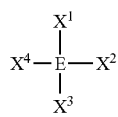

I wherein
E is phosphorus or nitrogen; and
$X^1$, $X^2$, $X^3$, and $X^4$ are independently selected from the group consisting of Ar and R, wherein at least one of $X^1$, $X^2$, $X^3$, and $X^4$ is an Ar group;
Ar is optionally substituted aryl, optionally substituted heteroaryl, and optionally substituted aralkyl; and
R is optionally substituted alkyl, optionally substituted alkenyl, optionally substituted alkynyl, optionally substituted haloalkyl, optionally substituted cycloalkyl, optionally substituted aralkyl, wherein at least one occurrence of R comprises at least one radioisotope.

The salts of the invention which comprise a cation of Formula I are suitable for use in imaging or assessment, particularly PET or SPECT imaging, of mitochondrial dysfunction in a patient. Preferred salts of the invention are labeled with one or more radioisotopes, preferably including $^{11}$C, $^{18}$F, $^{76}$Br, or $^{123}$I and more preferably $^{18}$F $^{76}$Br, or $^{123}$I. The invention provides a phosphonium cation tracer labeled with $^{11}$C-methyl group, e.g., [$^{11}$C]triphenylmethyl phosphonium (TPMP). Although suitable for use in medical centers situated at or near a cyclotron, the short half-life time of $^{11}$C, e.g., about 20 minutes, limits the use of [$^{11}$C]TPMP at distant medical centers. Preferred salts of the invention comprise a $^{18}$F, $^{76}$Br, $^{123}$I, or a combination thereof and are suitable for use in peripheral medical facilities and PET clinics.

The present invention provides lipophilic salts comprising a cation of Formula I or a subformula thereof which are preferentially taken up by dysfunctional mitochondria, e.g., mitochondria with suppressed or enhanced activity, and are suitable for use in imaging or radiotherapeutic applications. The invention provides imaging agents comprising a radiolabeled labeled lipophilic cations, particularly lipophilic phosphonium or ammonium salts of the invention which has one or more radioisotopes which is capable of binding to dysfunctional mitochondria, e.g., mitochondria with suppressed or enhanced activity. More particularly, the radiolabeled labeled lipophilic phosphonium or ammonium salts of the invention are suitable for use in measuring mitochondrial membrane potential ($\Delta\Psi$m) in vivo under a variety of conditions wherein the radiation emitted by the radioisotope of the lipophilic phosphonium or ammonium salt is utilized to form the image. In preferred embodiments, radiolabeled lipophilic phosphonium or ammonium salts of the invention comprise one or more radioisotopes capable of emitting positron radiation and are suitable for use in positron emission tomography (PET).

According to yet another aspect, the present invention provides pharmaceutical compositions comprising radiolabeled labeled salts of Formula I or the pharmaceutically acceptable salts or solvates thereof, which compositions are useful for the imaging variations in mitochondrial surface potential ($\Delta\Psi$m), cells or tissues having dysfunctional mitochondria, and diseases or disorders associated with dysfunctional mitochondria. The invention further provides methods of imaging patients suffering from any of the above-recited diseases or disorders with an effective amount of a salt or composition of the invention.

Additionally this invention relates to the use of the salts of the invention (particularly labeled salts of this invention emitting high energy radiation) as therapeutic agents for the treatment of diseases and disorders associated with dysfunctional mitochondria for which the lipophilic phosphonium or ammonium salts of the invention have high affinity, e.g., disorders or diseases associated with dysfunctional mitochondria activity. Typical disease and disorders include cancer, cardiovascular and liver diseases, degenerative disorders, autoimmune diseases and disorder, aging, DNA mutations, oxidative stress disorders, various myopaties, HIV, AIDS, and the like.

Preferred lipophilic cations, including phosphonium or ammonium salts, of the invention preferentially localize to cells possessing mitochondria with elevated or suppressed levels of activity, e.g., dysfunctional mitochondrial activity.

BRIEF DESCRIPTION OF THE DRAWING

FIGS. 1 through 19 show results of Examples 9 through 19 which follow.

DETAILED DESCRIPTION OF THE INVENTION

Figure 7:
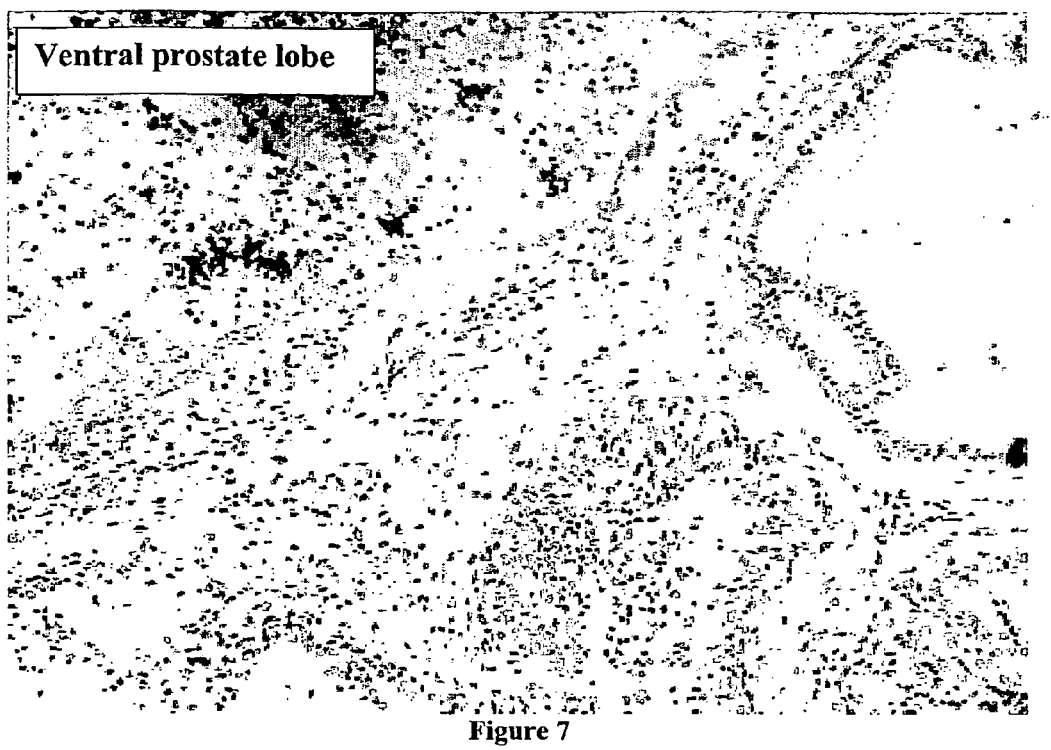

In addition to salts of Formula I, described above, the invention is further directed to lipophilic salts of Formula I (shown above) wherein the compounds provided by the invention are lipophilic salts of Formula I wherein Ar is optionally substituted aryl having from 6 to 18 carbon atoms and between 1 and 3 rings, optionally substituted heteroaryl having from 3 to about 18 carbon atoms, between 1 and about 3 rings and between 1 and about 4 ring heteroatoms selected from N, O, and S, and optionally substituted aralkyl having between 7 and about 12 carbon atoms; and R is optionally substituted $C_{1-6}$alkyl, optionally substituted $C_{2-6}$alkenyl, optionally substituted $C_{2-6}$alkynyl, optionally substituted $C_{1-6}$haloalkyl having at least one F, Cl, Br, or I atom, optionally substituted cycloalkyl having between 3 and about 8 ring carbon atoms, optionally substituted aralkyl having between 7 and about 12 carbon atoms, wherein at least one occurrence of R comprises at least one radioisotope.

Preferred salts of the invention include salts having at least one phophonium cation of Formula I where E is phosphorus. Other preferred salts of the invention include those having at least one ammonium cation of Formula I where E is nitrogen. Other preferred salts comprise a mixture of cations according to Formula I where each cation may be a phophonium or ammonium cation.

Preferred salts of the invention comprise at least one R substitutent which comprises a radioisotope capable of emitting positrons. Typically preferred positron emitting radioisotopes suitable for use in R substitutents include $^{11}$C, $^{18}$F, $^{123}$I or any combination thereof.

Other preferred salts provided by the invention include salts comprising a cation of Formula II:

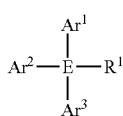

wherein

E is phosphorus or nitrogen; and $Ar^1$, $Ar^2$, and $Ar^3$ are independently selected from the group consisting of optionally substituted aryl, optionally substituted heteroaryl, and optionally substituted aralkyl; and $R^1$ is optionally substituted alkyl, optionally substituted alkenyl, optionally substituted alkynyl, optionally substituted haloalkyl, optionally substituted cycloalkyl, optionally substituted aralkyl, wherein at least one occurrence of R comprises at least one radioisotope.

More preferably, cations according to Formula II which are provided by the invention include those, wherein $Ar^1$, $Ar^2$, and $Ar^3$ are independently selected from the group consisting of optionally substituted aryl having from 6 to 18 carbon atoms and between 1 and 3 rings, optionally substituted heteroaryl having from 3 to about 18 carbon atoms, between 1 and about 3 rings and between 1 and about 4 ring heteroatoms selected from N, O, and S, and optionally substituted aralkyl having between 7 and about 12 carbon atoms; and $R^1$ is optionally substituted $C_{1-6}$alkyl, optionally substituted $C_{2-6}$alkenyl, optionally substituted $C_{2-6}$alkynyl, optionally substituted $C_{1-6}$haloalkyl having at least one F, Cl, Br, or I atom, optionally substituted cycloalkyl having between 3 and about 8 ring carbon atoms, optionally substituted aralkyl having between 7 and about 12 carbon atoms, wherein at least one occurrence of R comprises at least one radioisotope.

Particularly preferred cations of the invention according to Formula II comprise a $R^1$ group which is selected from the group consisting of $^{11}$C-methyl, optionally substituted $C_{1-6}$alkyl, optionally substituted $C_{7-12}$aralkyl, optionally substituted $C_{6-12}$aryl, each of which is substituted with one or more $^{11}$C-methyl, $^{11}$C-methoxy, $^{18}$F, $^{76}$Br, $^{123}$I, $^{125}$I, $^{131}$I, or a combination thereof More preferably, $R^1$ is $^{11}$C-methyl, $C_{2-6}$alkyl substituted with one or more $^{18}$F, or benzyl substituted with one or more $^{18}$F, $^{76}$Br, or $^{123}$I.

The invention also provides salts comprising at least one cation according to Formula I or Formula II wherein R or $R^1$ comprises one or more radioisotopes suitable for use in radiation therapy.

The present invention further provides salts comprising a cation of Formula I which is represented by Formula III:

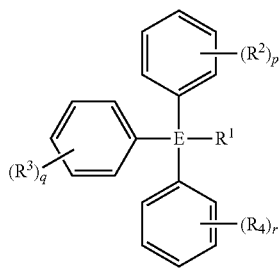

wherein

E is phosphorus or nitrogen;

$R^1$ is optionally substituted alkyl, optionally substituted alkenyl, optionally substituted alkynyl, optionally substituted haloalkyl, optionally substituted cycloalkyl, optionally substituted aralkyl, wherein at least one occurrence of R comprises at least one radioisotope;

$R^2$, $R^3$, and $R^4$ are independently selected at each occurrence of $R^2$, $R^3$, and $R^4$ from the group consisting of hydrogen, halogen, cyano, nitro, optionally substituted alkyl, optionally substituted alkenyl, optionally substituted alkynyl, optionally substituted alkoxy, optionally substituted (cycloalkyl)alkyl, optionally substituted alkylthio, optionally substituted alkylsulfinyl, or optionally substituted alkylsulfonyl, and optionally substituted mono or dialkylcarboxamide.

Preferred $R^1$ groups of Formula III include halo-$C_{2-6}$alkyl group or a halobenzyl group and more preferably $R^1$ of Formula III is selected from the group consisting ω-fluoro-$C_{2-6}$alkyl, ω-iodo-$C_{2-6}$alkyl group, ortho, meta or para-fluorobenzyl group, or ortho, meta or para-iodobenzyl group.

Other preferred salts of the invention having a cation according to Formula I include those salts which comprise a cation according to Formula IV:

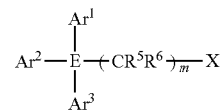

wherein

E is phosphorus or nitrogen;

$Ar^1$, $Ar^2$, and $Ar^3$ are independently selected from the group consisting of optionally substituted aryl, optionally substituted heteroaryl, and optionally substituted aralkyl; and $R^5$ and $R^6$ are independently selected at each occurrence of $R^5$ and $R^6$ from the group consisting of hydrogen, halogen, hydroxy, amino, optionally substituted alkyl, optionally substituted haloalkyl, and optionally substituted alkoxy;

X is $^{11}$C-methyl or a radioisotope of fluorine or iodine; and m is a number from about 2 to about 6.

Yet other preferred salts of the invention having a cation according to Formula I include those salts which comprise a cation according to Formula V:

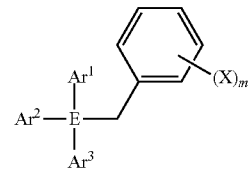

wherein

E is phosphorus or nitrogen;

$Ar^1$, $Ar^2$, and $Ar^3$ are independently selected from the group consisting of optionally substituted aryl, optionally substituted heteroaryl, and optionally substituted aralkyl; and X is $^{11}$C-methyl or a radioisotope of fluorine or iodine; and m is a number from about 1 to about 5.

Still other preferred salts of the invention having a cation according to Formula I include those salts which comprise a cation according to Formula VI:

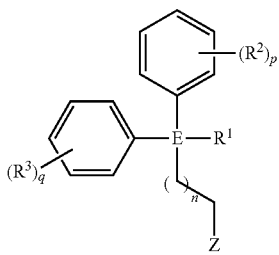

wherein
E is phosphorus or nitrogen;
Z is chloro, fluoro, hydroxy, or methoxy;
n is a number from 1 to about 12;
p and q are independently selected numbers from zero to about 5;
$R^1$ is optionally substituted alkyl, optionally substituted alkenyl, optionally substituted alkynyl, optionally substituted haloalkyl, optionally substituted cycloalkyl, optionally substituted aralkyl, wherein at least one occurrence of R comprises at least one radioisotope; and
$R^2$ and $R^3$ are independently selected at each occurrence of $R^2$ and $R^3$ from the group consisting of hydrogen, halogen, cyano, nitro, optionally substituted alkyl, optionally substituted alkenyl, optionally substituted alkynyl, optionally substituted alkoxy, optionally substituted (cycloalkyl)alkyl, optionally substituted alkylthio, optionally substituted alkylsulfinyl, or optionally substituted alkylsulfonyl, and optionally substituted mono or dialkylcarboxamide.

Other preferred salts of the invention having a cation according to Formula I include those salts which comprise a cation according to Formula VII

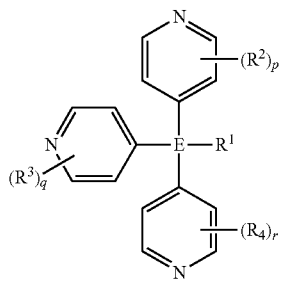

wherein
E is phosphorus or nitrogen;
p, q, and r are independently selected numbers from zero to about 4;
$R^1$ is optionally substituted alkyl, optionally substituted alkenyl, optionally substituted alkynyl, optionally substituted haloalkyl, optionally substituted cycloalkyl, optionally substituted aralkyl, wherein at least one occurrence of R comprises at least one radioisotope;
$R^2$, $R^3$, and $R^4$ are independently selected at each occurrence of $R^2$, $R^3$, and $R^4$ from the group consisting of hydrogen, halogen, cyano, nitro, optionally substituted alkyl, optionally substituted alkenyl, optionally substituted alkynyl, optionally substituted alkoxy, optionally substituted (cycloalkyl)alkyl, optionally substituted alkylthio, optionally substituted alkylsulfinyl, or optionally substituted alkylsulfonyl, and optionally substituted mono or dialkylcarboxamide.

Particularly preferred salts comprising at least one pharmaceutically acceptable anion and at least one cation according to Formula I include those salts comprising at least one cation selected from the group consisting of:
$^{11}$C-methyl-triphenylphosphonium ion;
$^{11}$C-methyl-tri-ortho-tolylphosphonium ion;
$^{11}$C-methyl-tri-meta-tolylphosphonium ion;
$^{11}$C-methyl-tri-para-tolylphosphonium ion;
$^{18}$F-2-fluoroethyl-triphenylphosphonium ion;
$^{18}$F-2-fluoroethyl-tri-ortho-tolylphosphonium ion;
$^{18}$F-2-fluoroethyl-tri-meta-tolylphosphonium ion;
$^{18}$F-2-fluoroethyl-tri-para-tolylphosphonium ion;
$^{18}$F-3-fluoropropyl-triphenylphosphonium ion;
$^{18}$F-3-fluoropropyl-tri-ortho-tolylphosphonium ion;
$^{18}$F-3-fluoropropyl-tri-meta-tolylphosphonium ion;
$^{18}$F-3-fluoropropyl-tri-para-tolylphosphonium ion;
$^{18}$F-4-fluorobutyl-triphenylphosphonium ion;
$^{18}$F-4-fluorobutyl-tri-ortho-tolylphosphonium ion;
$^{18}$F-4-fluorobutyl-tri-meta-tolylphosphonium ion;
$^{18}$F-4-fluorobutyl-tri-para-tolylphosphonium ion;
$^{18}$F-2-fluorobenzyl-triphenylphosphonium ion;
$^{18}$F-2-fluorobenzyl-tri-ortho-tolylphosphonium ion;
$^{18}$F-2-fluorobenzyl-tri-meta-tolylphosphonium ion;
$^{18}$F-2-fluorobenzyl-tri-para-tolylphosphonium ion;
$^{18}$F-3-fluorobenzyl-triphenylphosphonium ion;
$^{18}$F-3-fluorobenzyl-tri-ortho-tolylphosphonium ion;
$^{18}$F-3-fluorobenzyl-tri-meta-tolylphosphonium ion;
$^{18}$F-3-fluorobenzyl-tri-para-tolylphosphonium ion;
$^{18}$F-4-fluorobenzyl-triphenylphosphonium ion;
$^{18}$F-4-fluorobenzyl-tri-ortho-tolylphosphonium ion;
$^{18}$F-4-fluorobenzyl-tri-meta-tolylphosphonium ion;
$^{18}$F-4-fluorobenzyl-tri-para-tolylphosphonium ion;
$^{18}$F-3-fluoro-4-formyl-benzyl-triphenylphosphonium ion;
$^{18}$F-3-fluoro-4-formyl-benzyl-tri-ortho-tolylphosphonium ion;
$^{18}$F-3-fluoro-4-formyl-benzyl-tri-meta-tolylphosphonium ion;
$^{18}$F-3-fluoro-4-formyl-benzyl-tri-para-tolylphosphonium ion;
($^{18}$F-4-fluorobenzyl)-(2-chloroethyl)-diphenylphosphonium ion;
($^{18}$F-4-fluorobenzyl)-(3-chloropropyl)-diphenylphosphonium ion;
($^{18}$F-4-fluorobenzyl)-(4-chlorobutyl)-diphenylphosphonium ion;
($^{18}$F-4-fluorobenzyl)-(6-chloropentyl)-diphenylphosphonium ion;
($^{18}$F-4-fluorobenzyl)-(5-chlorohexyl)-diphenylphosphonium ion;
$^{18}$F-2-fluoroethyl-tri(4-pyridyl)phosphonium ion;
$^{18}$F-3-fluoropropyl-tri(4-pyridyl)phosphonium ion;
$^{18}$F-4-fluorobutyl-tri(4-pyridyl)phosphonium ion;
$^{18}$F-2-fluorobenzyl-tri(4-pyridyl)phosphonium ion;
$^{18}$F-3-fluorobenzyl-tri(4-pyridyl)phosphonium ion;
$^{18}$F-4-fluorobenzyl-tri(4-pyridyl)phosphonium ion; and
$^{18}$F-3-fluoro-4-formyl-benzyl-tri(4-pyridyl)phosphonium ion.

Preferred radiolabeled salts of the invention including those salts comprising a cation according to any one of Formula I, II, III, IV, V, VI, or VII, selectively localize to the mitochondria such that the ratio of radiation emitted from radiolabeled salts present in mitochondria to background radiation, e.g., radiolabeled salt not taken up in mitochondria is at least about 5:1. More preferably, salts of the invention are selectively taken up in dysfunctional mitochondria such that the ratio of to normal mitochondria is at least about 5:1.

The salts of the invention, particularly the lipophilic salts of the invention, have a distribution profile in the body which is a function of mitochondrial integrity and are suitable for use as diagnostic tools in the identification and imaging of various diseases and disorders associated with mitochondrial dysfunction. Moreover, the salts of the invention are useful diagnostic tools for assessing the efficacy of existing therapeutically drugs as well as the development of novel drugs. For example, the effectiveness of drugs that trigger apoptosis (e.g., anticancer drugs) or suppress apoptosis (e.g., drugs that block the degenerative process in HIV) can be assessed by determining if the administration of said drugs can be monitored by observing the change (effective) or effective) to $\Delta\Psi m$ by measuring $\Delta\Psi m$ using the salts and imaging methods of the invention.

Preferred compounds of the invention, particularly compounds suitable for use in the imaging methods provided by the invention, include one or more radioisotopes capable of emitting one or more forms of radiation which are suitable for detection with any standard radiology equipment such as PET, SPECT, gamma cameras, MRI and the like. Preferred radioisotopes include tritium and isotopes of carbon, fluorine, technetium, iodine and other isotopes capable of emitting positrons. Particularly preferred radioisotopes include $^{11}C$, $^{18}F$, $^{76}Br$, and $^{123}I$.

The present invention further provides method of imaging which comprise the steps of:
    providing at least one radiolabeled salt comprising a pharmaceutically acceptable anion and at least one cation according to any one of Formula I, II, III, IV, V, VI, or VII;
    contacting cells or tissues with the radiolabeled salt; and
    making a radiographic image.

The imaging methods provided by the invention are suitable for assessing mitochondrial membrane potential ($\Delta\Psi m$). More particularly, the imaging methods of the present invention are suitable for measuring change in mitochondrial membrane potential over time to assess the efficacy of therapeutic protocols or pharmaceutical treatments. Cells which exhibit suppressed or enhanced rates of apoptosis frequently also exhibit decreased or increased mitochondria activity. The salts provided by the present invention typically localize to cells in a concentration proportional to the level of mitochondria activity. Thus frequently when cells are experiencing reduced levels of apoptosis (e.g., cancer cells), a greater portion of the salt of the invention administered to the patient localizes to those cells, and vice versa, cells with enhanced levels of apoptosis (e.g., auto immune disorders, tumor cells responsive to chemotherapy agents) will accumulate less salt of the invention than normal cells. Thus the imaging methods of the present invention are suitable for use in imaging of cells, tissues or other physiological targets which are experiencing suppressed or enhanced apoptosis.

The imaging methods of the present invention are generally suitable for imaging of any disease, disorder, or pathology which is related to mitochondria. Preferred diseases and disorders which are suitable for imaging include cancer (including neoplasms), cardiovascular diseases (including infraction and perfusion), liver diseases, degenerative diseases or disorders, autoimmune disorders, aging, HIV infections, myopathies caused by oxidative stress or DNA mutation, or diseases and disorders associated with mitochardial dysfunction.

The imaging methods of the invention are also suitable for use in assessing efficacy of therapeutic drugs capable of triggering or suppressing apoptosis. The imaging methods of the invention may also be used to assess the efficacy of chemotherapy or radiation treatment protocols used to retard or destroy cancer and other malignant tumors.

The imaging methods of the invention which are suitable for assessing the efficacy of a therapeutic drug are also suitable in developing new therapeutic agents which are capable of disrupting mitochondrial function in target tissue.

The radiolabeled lipophilic salts of the invention and imaging methods using same provide a non-invasive approach for early and sensitive assessment of treatment efficacy within a few days of starting a therapeutic protocol compared to current assessment methods which may require months. Most major anticancer drugs (e.g., taxol, cisplatin, vinblastine, and etoposide) induce their apoptotic effect via a cascade of events in which the collapse of $\Delta\Psi m$ constitutes an early, obligatory and irreversible step of the apoptotic process. Radiolabeled lipophilic salts of the invention accumulate mainly in the mitochondria and in direct correlation with $\Delta\Psi m$. Cells affected by the treatment will accumulate radiolabeled lipophilic salts of the invention much less than non-affected cells. Therefore, significant change between pre- and post-treatment scan will indicate tumor responding to treatment and lack of differences will indicate non-responding tumors. Collapse of $\Delta\Psi m$ occurs within hours after treatment with most therapeutic agents.

The ability to monitor the first event of the irreversible phase of the apoptotic process affords a noninvasive method for early and sensitive detection of tumor response to treatment. In the clinical setting, the imaging methods provided by the present invention offer a powerful tool for tailoring of chemotherapy strategies that will most benefit the patient with reduced morbidity.

The radiolabeled lipophilic salts of the invention are also suitable for use in developing these new generations of chemotherapy agents. The radiolabeled lipophilic salts of the invention and imaging methods of using the same are suitable for use as non-invasive technique for an early and sensitive assessment at the molecular level of treatment efficacy in clinical studies. Moreover the imaging methods of the invention are suitable for use in selecting suitable malignant targets in test subjects, based on the functional integrity of mitochondria, upon which the novel drug can be tested.

The present invention further provides imaging methods suitable for use in the imaging of tumors with one or more salts having a cation according to Formula I or a subformula thereof. In preferred tumor imaging methods of the invention, the radiolabeled salt administered to a patient preferentially accumulates in mitochondria of malignant cells such that the concentration of radiolabeled cation of Formula I is greater in the mitochondria of the malignant cell than the concentration of the cation in adjacent normal cells.

The extent of cancerous disease (stage) is a major prognostic factor and non-invasive staging using imaging technologies has a key role in design of treatment strategies (e.g., surgery vs. radio-chemotherapy vs. adjuvant chemotherapy). The lipophilic salts of the present invention including salts having a cation according to Formula I accumulate in malignant cells to a substantially greater extent than in normal cells. Administration of a radiolabeled salt of the present invention is suitable for the identification and imaging of malignant cells and tumors and is further suitable for measuring the stage of tumor development.

The tumor imaging methods of the invention are particularly suitable in certain embodiments for imaging of cancers, more particularly for imaging neoplasms including a variety of lung, breast, and prostate cancers. Moreover, the tumor imaging method of the invention may be used is capable of determining the extent of the cancerous disease (cancer stage).

The present invention provides methods of differentiating between malignant tumors, such as neoplasms, and tissue suffering from a variety of inflammation processes. The lipophilic salts of the invention including salts having a cation of Formula I accumulate in malignant cells to a greater extent than in normal cells and accumulate in cellular components of inflammatory processes to a lesser extent than in normal cells such that a differential distinction can be made between malignant cells, normal cells and cells suffering from inflammation. Differential detection of malignancy will obviate the numerous unnecessary surgeries conducted each year and improve the cost-effectiveness of care management in oncology.

The tumor imaging methods of the present invention are capable of distinguishing between tissue suffering from an inflammatory process and malignant lesions. While not wishing to be bound by theory, differential detection of malignant cells is possible because malignant cells have a greater accumulation of the salts of the invention than normal cells and tissues or cellular components of inflammatory processes typically accumulate a lower concentration of the salts of the invention. Thus the concentration of any salt of the invention in the malignant lesion is significantly greater than normal tissue and tissue suffering from an inflammatory process.

The present invention further provides methods of imaging cardiovascular diseases, particularly methods of imaging the myocardia The cardiovascular imaging methods of the invention comprise the administration of at least one compound according to Formula I, or a subformula thereof to a patient suffering from or susceptible to a cardiovascular disease.

[18F]phosphonium cations of the invention are suitable for various cardiovascular diseases, particularly myocardial imaging. Myocytes contain the highest concentration of mitochondria and therefore the heart is by far the major organ target of phosphonium cations. In addition, phosphonium cation maintain excellent perfusion characteristics permitting high-contrast imaging of the heart Infarct and heart failure involve apoptosis followed by necrosis processes. [$^{18}$F]Phosphonium cations are capable to accurately distinguish between myocardial segments in which the apoptotic process cannot be stopped by medication and revascularization, and myocardial area that can be salvaged by intervention.

Preferred imaging methods provided by the invention include the use of lipophilic salts according to any one of Formula I, II, III, IV, V, VI, or VII which are capable of generating at least a 2:1 target to background ratio of radiation intensity, or more preferably about a 5:1, about a 10:1 or about a 15:1 ratio of radiation intensity between target and background. In certain preferred methods the radiation intensity of the target tissue is more intense than that of the background. In other embodiments, the invention provides methods where the radiation intensity of the target tissue is less intense than that of the background. Generally, any difference in radiation intensity between the target tissue and the background which is sufficient to allow for identification and visualization of the target tissue is sufficient for use in the methods of the present invention.

In preferred methods of the invention the compounds of the invention are excreted from tissues of the body quickly to prevent prolonged exposure to the radiation of the radiolabeled compound administered to the patient. Typically compounds according to Formula I or any subformula thereof are eliminated from the body in less than about 24 hours. More preferably, compounds of the invention are eliminated from the body in less than about 16 hours, 12 hours, 8 hours, 6 hours, 4 hours, 2 hours, 90 minutes, or 60 minutes. Typically preferred compounds are eliminated in between about 60 minutes and about 120 minutes.

Preferred compounds of the invention are stable in vivo such that substantially all, e.g., more than about 50%, 60%, 70%, 80%, or more preferably 90% of the injected compound is not metabolized by the body prior to excretion.

Compounds and salts of the invention and imaging methods of the invention are useful in imaging a variety of conditions including cancer, cardiovascular and liver diseases, HIV, AIDS, autoimmune disease, degenerative disorders, neoplasms, and the like.

Typical subjects to which compounds of the invention may be administered will be mammals, particularly primates, especially humans. For veterinary applications, a wide variety of subjects will be suitable, e.g. livestock such as cattle, sheep, goats, cows, swine and the like; poultry such as chickens, ducks, geese, turkeys, and the like; and domesticated animals particularly pets such as dogs and cats. For diagnostic or research applications, a wide variety of mammals will be suitable subjects including rodents (e.g. mice, rats, hamsters), rabbits, primates, and swine such as inbred pigs and the like. Additionally, for if vitro applications, such as in vitro diagnostic and research applications, body fluids and cell samples of the above subjects will be suitable for use such as mammalian, particularly primate such as human, blood, urine or tissue samples, or blood urine or tissue samples of the animals mentioned for veterinary applications.

The present invention also provide packaged pharmaceutical compositions comprising a pharmaceutical acceptable carrier and a salt comprising at least one pharmaceutically acceptable anion and a cation according to any one of Formula I, II, III, IV, V, VI, or VII. In certain embodiments the packaged pharmaceutical composition will comprise the reaction precursors necessary generate the compound or salt according to Formula I or subformula thereof upon combination with a radiolabeled precursor. Other packaged pharmaceutical compositions provided by the present invention further comprise indicia comprising at least one of:

instructions for using the composition to image cells or tissues having increased or suppressed mitochondrial activity, or instructions for using the composition to assess therapeutic effect of a drug protocol administered to a patient, or instructions for using the composition to selectively image malignant cells and tumors in the presence of inflammation, or instructions for using the composition to measure mitochondrial membrane potential ($\Delta\Psi m$).

In certain preferred embodiments, the invention provides a kit according to the invention contains from about 1 to about 30 mCi of the radionuclide-labeled imaging agent described above, in combination with a pharmaceutically acceptable carrier. The imaging agent and carrier may be provided in solution or in lyophilized form. When the imaging agent and carrier of the kit are in lyophilized form, the kit may optionally contain a sterile and physiologically acceptable reconstitution medium such as water, saline, buffered saline, and the like.

The present invention further provides apparatus and synthetic protocols for the automated synthesis of $^{11}$C, $^{18}$F, $^{76}$Br, or $^{123}$I labeled salts of the invention, including salts comprising a cation according to any one of Formula I, II, III, VI, V, VII, and VII, and preparation of pharmaceutical compositions comprising same. The half-life (120 min) of F-18 allows for distribution of cationic probes from central cyclotron to satellite PET scanners, similarly to the rapidly evolving distribution system adopted for [18F]FDG. Tagging the cationic probes with I-123 will allow for distribution from a manufacturing center to medical institutions equipped with SPECT.

Imaging agents of the invention may be used in accordance with the methods of the invention by one of skill in the art, e.g., by specialists in nuclear medicine, to image sites having a dysfunctional mitochondria, e.g., mitochondria exhibiting aberrant activity, in a subject or patient. Any site having a dysfunctional mitochondria, e.g., mitochondria exhibiting aberrant activity, may be imaged by the imaging methods and imaging agents of the present invention.

Images can be generated by virtue of differences in the spatial distribution of the imaging agents which accumulate at a site having a dysfunctional mitochondria, e.g., mitochondria exhibiting aberrant activity. The spatial distribution may be measured using any means suitable for the particular label, for example, a gamma camera, a PET apparatus, a SPECT apparatus, and the like. The extent of accumulation of the imaging agent may be quantified using known methods for quantifying radioactive emissions. A particularly useful imaging approach employs more than one imaging agent to perform simultaneous studies. Alternatively, the imaging method may be carried out a plurality of times with increasing administered dose of the salt according to Formula I to perform successive studies using the split-dose image subtraction method.

Preferably, a detectably effective amount of the imaging agent of the invention is administered to a subject. In accordance with the invention, "a detectably effective amount" of the imaging agent of the invention is defined as an amount sufficient to yield an acceptable image using equipment which is available for clinical use. A detectably effective amount of the imaging agent of the invention may be administered in more than one injection. The detectably effective amount of the imaging agent of the invention can vary according to factors such as the degree of susceptibility of the individual, the age, sex, and weight of the individual, idiosyncratic responses of the individual, the dosimetry. Detectably effective amounts of the imaging agent of the invention can also vary according to instrument and film-related factors. Optimization of such factors is well within the level of skill in the art.

The amount of imaging agent used for diagnostic purposes and the duration of the imaging study will depend upon the radionuclide used to label the agent, the body mass of the patient, the nature and severity of the condition being treated, the nature of therapeutic treatments which the patient has undergone, and on the idiosyncratic responses of the patient. Ultimately, the attending physician will decide the amount of imaging agent to administer to each individual patient and the duration of the imaging study.

The compounds herein described may have one or more asymmetric centers or planes. Compounds of the present invention containing an asymmetrically substituted atom may be isolated in optically active or racemic forms. It is well known in the art how to prepare optically active forms, such as by resolution of racemic forms (racemates), by asymmetric synthesis, or by synthesis from optically active starting materials. Resolution of the racemates can be accomplished, for example, by conventional methods such as crystallization in the presence of a resolving agent, or chromatography, using, for example a chiral HPLC column. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral (enantiomeric and diastereomeric), and racemic forms, as well as all geometric isomeric forms of a structure are intended, unless the specific stereochemistry or isomeric form is specifically indicated.

When any variable occurs more than one time in any constituent or formula for a compound, its definition at each occurrence is independent of its definition at every other occurrence. Thus, for example, if a group is shown to be substituted with 0-2 R*, then said group may optionally be substituted with up to two R* groups and R* at each occurrence is selected independently from the definition of R*. Also, combinations of substituents and/or variables are permissible only if such combinations result in stable compounds.

As indicated above, various substituents of the various formulae (compounds of Formula I, II, III, IV, V, VI, or VII) are "optionally substituted", including Ar, $Ar^1$, $Ar^2$, $Ar^3$, R, $R^1$, $R^2$, $R^3$, $R^4$, $R^5$, $R^6$, X, $X^1$, $X^2$, $X^3$, $X^4$, and Z of Formula I, II, III, IV, V, VI and VII, and such substituents as recited in the sub-formulae such as Formula I and subformulae. The term "substituted," as used herein, means that any one or more hydrogens on the designated atom or group is replaced with a selection from the indicated group of substituents, provided that the designated atom's normal valence is not exceeded, and that the substitution results in a stable compound. When a substituent is oxo (keto, i.e., =O), then 2 hydrogens on an atom are replaced. The present invention is intended to include all isotopes (including radioisotopes) of atoms occurring in the present compounds.

When substituents such as Ar, $Ar^1$, $Ar^2$, $Ar^3$, R, $R^1$, $R^2$, $R^3$, $R^4$, $R^5$, $R^6$, X, $X^1$, $X^2$, $X^3$, $X^4$, and Z of Formula I and subformulae thereof, and such substituents as recited in the sub-formulae are further substituted, they may be so substituted at one or more available positions, typically 1 to 3 or 4 positions, by one or more suitable groups such as those disclosed, herein. Suitable groups that may be present on a "substituted" $R^1$, $R^2$, R or other group include e.g., halogen; cyano; hydroxyl; nitro; azido; alkanoyl (such as a $C_{1-6}$ alkanoyl group such as acyl or the like); carboxamido; alkyl groups (including cycloalkyl groups, having 1 to about 8 carbon atoms, preferably 1, 2, 3, 4, 5, or 6 carbon atoms); alkenyl and alkynyl groups (including groups having one or more unsaturated linkages and from 2 to about 8, preferably 2, 3, 4, 5 or 6, carbon atoms); alkoxy groups having one or more oxygen linkages and from 1 to about 8, preferably 1, 2, 3, 4, 5 or 6 carbon atoms; aryloxy such as phenoxy; alkylthio groups including those having one or more thioether linkages and from 1 to about 8 carbon atoms, preferably 1, 2, 3, 4, 5 or 6 carbon atoms; alkylsulfinyl groups including those having one or more sulfinyl linkages and from 1 to about 8 carbon atoms, preferably 1, 2, 3, 4, 5, or 6 carbon atoms; alkylsulfonyl groups including those having one or more sulfonyl linkages and from 1 to about 8 carbon atoms, preferably 1, 2, 3, 4, 5, or 6 carbon atoms; aminoalkyl groups including groups having one or more N atoms and from 1 to about 8, preferably 1, 2, 3, 4, 5 or 6, carbon atoms; carbocyclic aryl having 6 or more carbons and one or more rings, (e.g., phenyl, biphenyl, naphthyl, or the like, each ring either substituted or unsubstituted aromatic); arylalkyl having 1 to 3 separate or fused rings and from 6 to about 18 ring carbon atoms, with benzyl being a preferred arylalkyl group; arylalkoxy having 1 to 3 separate or fused rings and from 6 to about 18 ring carbon atoms, with O-benzyl being a preferred arylalkoxy group; or a saturated, unsaturated, or aromatic heterocyclic group having 1 to 3 separate or fused rings with 3 to about 8 members per ring and one or more N, O or S atoms, e.g. coumarinyl, quinolinyl, isoquinolinyl, quinazolinyl, pyridyl, pyrazinyl, pyrimidyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such heterocyclic groups may be further substituted, e.g. with hydroxy, alkyl, alkoxy, halogen and amino.

As used herein, "alkyl" is intended to include both branched and straight-chain saturated aliphatic hydrocarbon groups, having the specified number of carbon atoms. Examples of alkyl include, but are not limited to, methyl, ethyl, n-propyl, i-propyl, n-butyl, s-butyl, t-butyl, n-pentyl, and s-pentyl. Preferred alkyl groups are $C_{1-6}$ alkyl groups. Especially preferred alkyl groups are methyl, ethyl, propyl, butyl, and 3-pentyl. The term $C_{1-4}$ alkyl as used herein includes alkyl groups consisting of 1 to 4 carbon atoms, which may contain a cyclopropyl moiety. Suitable examples are methyl, ethyl, and cyclopropylmethyl.

"Cycloalkyl" is intended to include saturated ring groups, having the specified number of carbon atoms, such as cyclopropyl, cyclobutyl, cyclopentyl, or cyclohexyl. Cycloalkyl groups typically will have 3 to about 8 ring members.

In the term "$(C_{3-8}$ cycloalkyl)$C_{1-4}$ alkyl", cycloalkyl, and alkyl are as defined above, and the point of attachment is on the alkyl group. This term encompasses, but is not limited to, cyclopropylmethyl, cyclohexylmethyl, and cyclohexylmethyl.

"Alkenyl" is intended to include hydrocarbon chains of either a straight or branched configuration comprising one or more unsaturated carbon-carbon bonds, which may occur in any stable point along the chain, such as ethenyl and propenyl. Alkenyl groups typically will have 2 to about 8 carbon atoms, more typically 2 to about 6 carbon atoms.

"Alkynyl" is intended to include hydrocarbon chains of either a straight or branched configuration comprising one or more carbon-carbon triple bonds, which may occur in any stable point along the chain, such as ethynyl and propynyl. Alkynyl groups typically will have 2 to about 8 carbon atoms, more typically 2 to about 6 carbon atoms.

"Haloalkyl" is intended to include both branched and straight-chain saturated aliphatic hydrocarbon groups having the specified number of carbon atoms, substituted with 1 or more halogen atoms. Examples of haloalkyl include, but are not limited to, mono-, di-, or tri-fluoromethyl, mono-, di-, or tri-chloromethyl, mono-, di-, tri-, tetra-, or penta-fluoroethyl, and mono-, di-, tri-, tetra-, or penta-chloroethyl. Typical haloalkyl groups will have 1 to about 8 carbon atoms, more typically 1 to about 6 carbon atoms.

"Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Alkoxy groups typically have 1 to about 8 carbon atoms, more typically 1 to about 6 carbon atoms.

"Halolkoxy" represents a haloalkyl group as defined above with the indicated number of carbon atoms attached through an oxygen bridge.

As used herein, the term "alkylthio" includes those groups having one or more thioether linkages and preferably from 1 to about 8 carbon atoms, more typically 1 to about 6 carbon atoms.

As used herein, the term "alkylsulfinyl" includes those groups having one or more sulfoxide (SO) linkage groups and typically from 1 to about 8 carbon atoms, more typically 1 to about 6 carbon atoms.

As used herein, the term "alkylsulfonyl" includes those groups having one or more sulfonyl ($SO_2$) linkage groups and typically from 1 to about 8 carbon atoms, more, typically 1 to about 6 carbon atoms.

As used herein, the term "alkylamino" includes those groups having one or more primary, secondary and/or tertiary amine groups and typically from 1 to about 8 carbon atoms, more typically 1 to about 6 carbon atoms.

"Halo" or "halogen" as used herein refers to fluoro, chloro, bromo, or iodo; and "counter-ion" is used to represent a small, negatively charged species such as chloride, bromide, hydroxide, acetate, sulfate, and the like.

As used herein, "carbocyclic group" is intended to mean any stable 3- to 7-membered monocyclic or bicyclic or 7- to 13-membered bicyclic or tricyclic group, any of which may be saturated, partially unsaturated, or aromatic. In addition to those exemplified elsewhere herein, examples of such carbocycles include, but are not limited to, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, phenyl, naphthyl, indanyl, and tetrahydronaphthyl.

As used herein, the term "heterocyclic group" is intended to include saturated, partially unsaturated, or unsaturated (aromatic) groups having 1 to 3 (preferably fused) rings with 3 to about 8 members per ring at least one ring containing an atom selected from N, O or S. The nitrogen and sulfur heteroatoms may optionally be oxidized. The term or "heterocycloalkyl" is used to refer to saturated heterocyclic groups.

The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. As used herein, the term "aromatic heterocyclic system" is intended to include any stable 5- to 7-membered monocyclic or 10- to 14-membered bicyclic heterocyclic aromatic ring system which comprises carbon atoms and from 1 to 4 heteroatoms independently selected from the group consisting of N, O and S. It is preferred that the total number of S and O atoms in the aromatic heterocycle is not more than 2, more preferably not more than 1.

Examples of heterocycles include, but are not limited to, those exemplified elsewhere herein and further include acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Preferred heterocyclic groups include, but are not limited to, pyridinyl, pyrimidinyl, furanyl, thienyl, pyrrolyl, pyrazolyl, pyrrolidinyl, morpholinyl, piperidinyl, piperazinyl, and imidazolyl. Also included are fused ring and spiro compounds containing, for example, the above heterocycles.

As used herein, the term "carbocyclic aryl" includes groups that contain 1 to 3 separate or fused rings and from 6 to about 18 ring atoms, without hetero atoms as ring members. Specifically preferred carbocyclic aryl groups include phenyl, and naphthyl including 1-napthyl and 2-naphthyl.

A "pharmaceutically acceptable carrier" refers to a biocompatible solution, having due regard to sterility, pH, isotonicity, stability, and the like and can include any and all solvents, diluents (including sterile saline, Sodium Chloride Injection, Ringer's Injection, Dextrose Injection, Dextrose and Sodium Chloride Injection, Lactated Ringer's Injection and other aqueous buffer solutions), dispersion media, coatings, antibacterial and antifungal agents, isotonic agents, and the like. The pharmaceutically acceptable carrier may also contain stabilizers, preservatives, antioxidants, or other additives, which are well known to one of skill in the art, or other vehicle as known in the art.

As used herein, "pharmaceutically acceptable salts" refer to derivatives of the disclosed compounds wherein the parent compound is modified by making non-toxic acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, malefic, hydroxymaleic, phenylacetic, glutamic, benzoic, salicylic, mesylic, sulfanilic, 2-acetoxybenzoic, fumaric, toluenesulfonic, methanesulfonic, ethane disulfonic, oxalic, isethionic, HOOC—$(CH_2)n$—COOH where n is 0-4, and the like. The pharmaceutically acceptable salts of the present invention can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts may be found, e.g., in *Remington's Pharmaceutical Sciences,* 17th ed., Mack Publishing Company, Easton, Pa., p. 1418 (1985).

Because of the correlation between elevated or suppressed mitiochondia activity and a variety of diseases and disorders, an imaging agent and methods of imaging using same that can assessing changes in mitochondria surface potential is an effective diagnostic tool for testing for the presence of a variety of disease states associated with triggering or suppressing apoptosis in cells. Moreover, imaging agents suitable for use in imaging or assessing changes in mitochondria surface potential are suitable for use in studying a variety of diseases including cancer, cardiovascular or liver diseases, HIV, AIDS, autoimmune disease, degenerative disorders, neoplasms, and the like.

EXAMPLES

The present invention is further illustrated by the following examples which should not be construed as limiting in any way. The contents of all cited references (including literature references, issued patents, published patent applications) as cited throughout this application are hereby expressly incorporated by reference. The practice of the present invention will employ, unless otherwise indicated, conventional techniques, which are within the skill of the art. Such techniques are explained fully in the literature.

Example 1

[$^{18}$F]3-fluoropropyltriphenyl-phosphonium ion ([$^{18}$F]FPTP)

The synthesis starts with the [$^{18}$F]fluoride from the cyclotron target transferred onto an anion exchange column (Trap and Release column (DW-TRC) D and W, Inc., Oakdale, Tenn., USA). The column is eluted with aqueous potassium carbonate (2.3 mg dissolved in 0.3 mL) into a 5 cc v-vial containing Kryptofix. The Kryptofix, potassium carbonate, [$^{18}$F]fluoride mixture is dried at 120 C; and, 7 mg of propyl ditosylate (Aldrich) is added in 0.5 mL acetonitrile. After heating at 80° C. for 5 minutes, 21 mg of triphenylphosphine (Aldrich) in 0.5 mL of toluene is added. The acetonitrile is evaporated away and the toluene mixture heated to boiling for 3-5 minutes. After evaporating the toluene and cooling the vial, 0.5 mL of high-pressure liquid chromatography (HPLC) solvent [35:65 acetonitrile:water (0.1 M ammonium formate)] is added to the vial. The mixture is filtered through a 0.45 µm Teflon HPLC filter (Alltech 13 mm) and injected onto a preparative HPLC column (Waters Novapak C-18 6 µm, 7.8×300 mm) at 7 ml/min for purification. The product is collected on a rotary evaporator modified to allow addition and removal of solvents, the HPLC solvent evaporated and the radiolabeled phosphonium salt dissolved in sterile normal saline. The overall decay corrected radiochemical yield of [18F]FPTP calculated from starting [18F]fluoride is 12 percent. After sterile filtration (PALL-Gelman 0.2 µm Tuffryn) into a sterile vial, the solution is checked for radiochemical, chemical purity and specific activity by analytical HPLC [40:60 acetonitrile:water (0.1 M ammonium formate), Waters Novapak C-18 60 Å4 µm, 3.9×150 mm] at 3 ml/min with a known concentration of cold standard characterized solution of 3-fluoropropyltriphenyl-phosphonium bromide [physical data: mp 313-316 C; $^1$H NMR (CDCl$_3$, δ) 1.81-2.17 (m, 2H), 4.01-4.11 (m, 2H), 4.72-4.75 (m, 1H), 4.87-4.90 (m, 1H), 7.69-7.88 (m, 15H)]. The synthesis is summarized in Scheme 1.

Scheme 1:
Synthesis of [$^{18}$F]alkyl phosphonium ions.

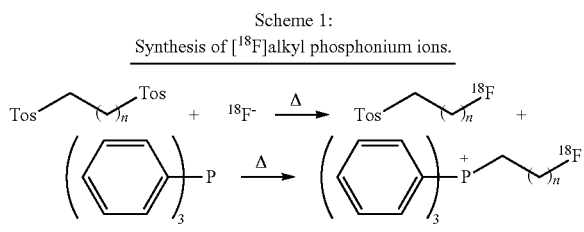

Example 2

[$^{18}$F]2-fluoroethyltriphenyl-phosphonium ion ([$^{18}$F]FETP)

[$^{18}$F]FETP was prepared according to the method used to prepare [$^{18}$F]FPTP as described in Example 1 supra.

Example 3

[$^{18}$F]2-fluorobutyltriphenyl-phosphonium ion ([$^{18}$F]FBTP)

[$^{18}$F]FBTP was prepared according to the method used to prepare [$^{18}$F]FPTP as described in Example 1 supra.

Example 4

[$^{18}$F]fluorobenzyltriphenyl-phosphonium ion

After collecting and drying the [$^{18}$F]fluoride in the potassium carbonate/Kryptofix (as described in Example 1), trimethylammnoniumbenzaldehyde triflate salt (7 mg) in 0.2 mL of dimethylsulfoxide(vacuum distilled from barium oxide prior to use) is added to the mixture. After heating at 120° C. for 5 minutes, the aldehyde is diluted with 5 mL of HPLC water and collected on a C-18 solid phase extraction cartridge (Waters C-18 Plus Sep-Pak) then washed with 10 ml of HPLC water and dried by inert gas flow through the cartridge for 3 minutes. The aldehyde is eluted from the cartridge with 2 mL of diethylether (Aldrich) and passed through 10% sodium borohydride on basic alumina (Aldrich-200-400 mg) to reduce it to the alcohol. The alcohol is subsequently converted to [$^{18}$F]fluorobenzyl bromide by mixing with triphenylphosphine dibromide (75-100 mg) in 1 mL of methylene chloride for 5 minutes. After passing through a silica solid phase extraction cartridge (Waters Silica Classic Sep-Pak) and washing with 1 mL of methylene chloride, the [$^{18}$F] fluorinated benzyl bromide is added to 21 mg of triphenylphosphine (or its analog) dissolved in 0.5 mL toluene in a 5 ml v-vial. The methylene chloride/ether solvent is evaporated away at low heat with inert gas flow, the vial capped and heated to boiling for 3-5 minutes. After evaporating the toluene and cooling the vial, 0.5 mL of high-pressure liquid chromatography (HPLC) solvent [50:50 acetonitrile:water (0.1 M ammonium formate)] is added to the vial. The mixture is filtered through a 0.45 µm Teflon HPLC filter (Alltech 13 mm) and injected onto a preparative HPLC column (Waters Novapak C-18 6 µm, 7.8×300 mm) at 7 ml/min for purification. The product is collected on a rotary evaporator modified to allow addition and removal of solvents, the HPLC solvent evaporated and the radiolabeled phosphonium salt dissolved in sterile normal saline. After sterile filtration (PALL-Gelman 0.2 µm Tuffryn) into a sterile vial, the solution is checked for radiochemical, chemical purity and specific activity by analytical HPLC [40:60 acetonitrile:water (0.1 M ammonium formate), Waters Novapak C-18 60 Å 4 µm, 3.9×150 mm] at 3 ml/min and compared to a known standard of p-fluorobenzyltriphenylphosphonium ion as in example 1. The overall decay corrected radiochemical yield of [18F]fluorbenzyltriphenyl phosphonium ion calculated from starting [18F] fluoride is 14 percent. [Physical Data: mp 313-316 C; $^1$H NMR (D$^6$-dmso, δ) 5.17-5.21 (d, 2H), 6.99-7.08 (m, 4H), 7.67-7.94 (m, 15H)]. The synthesis is summarized in Scheme 2.

Scheme 2:
Synthesis of [$^{18}$F]aryl phosphonium ions.

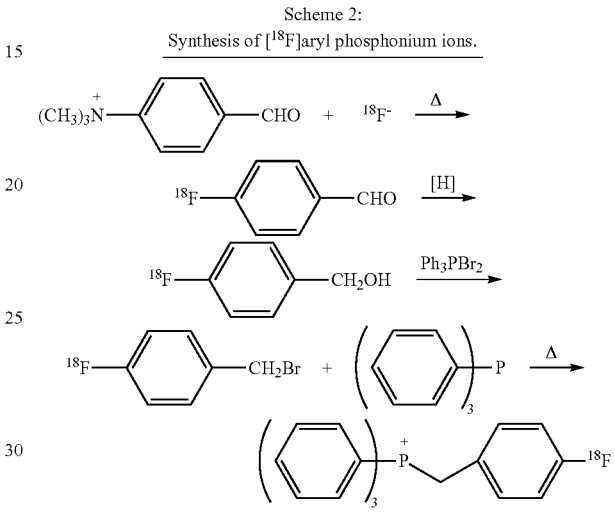

Example 5

Radiolabeled diphenyl(haloalkyl)([$^{18}$F]fluorobenzyl) phosphonium ion

Radiolabeled haloalkylphosphonium ion derivatives are prepared by the synthesis of a $^{18}$F-fluorobenzyl halide as described in Example 4. The radiolabeled benzyl halide will be attached to diphenylphosphine to create a radiolabeled phosphine: Next the radiolabeled phosphine will be converted to the haloalkylphosphonium ion by reaction with the appropriate haloalkyl iodide. The synthesis of the radiolabeled chloroalkyl phosphonium ion is summarized in Scheme 3. Other haloalkyl species including chloro, bromo and iodo attached to alkyl chains of varying length, branching and site of halide substitution can also be prepared.

Scheme 3:
synthesis of the [$^{18}$F]-benzyl-chloroalkyl phosphonium ion.

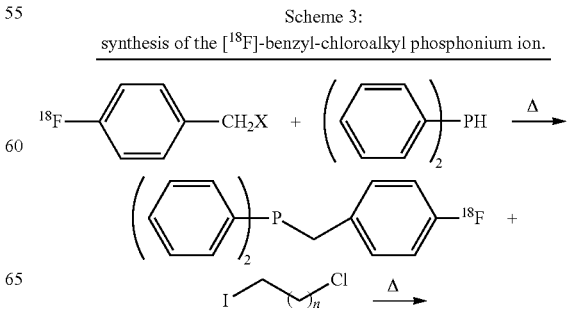

-continued

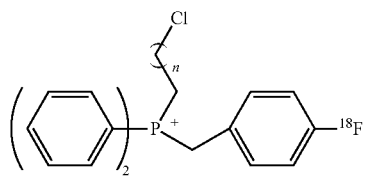

Example 6 radiolabled [¹⁸F]fluoroalkyl-tripyridylphosphonium ion and radiolabled [¹⁸F]fluorobenzyl-tripyridylphosphonium ion Radiolabeled phosphonium ions containing pyridyl rings are prepared according to the generalized reaction scheme provided in Scheme 4. The radiosynthesis involves the reaction of ¹⁸F-fluoroalkyl (Example 1) and benzyl (Example 4) moieties as described above with tripyridylphosphine.

Scheme 4:
synthesis of [¹⁸F]-alkyl or aryl tripyridylphosphonium ion

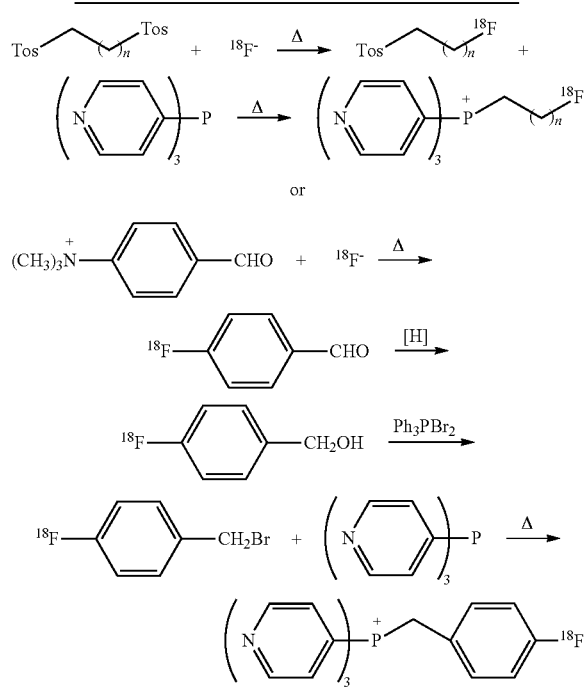

Example 7

Radiolabeled Ammonium Ions

The procedures described in Examples 1-6 for preparation of radiolabeled phosphonium ions are also applicable for the preparation of quaternary ammonium ions as illustrated in Scheme 5. Quaternary ammonium ions have comparable biodistribution to phosphonium ions.

Scheme 5:
synthesis of radiolabeled ammonium ions

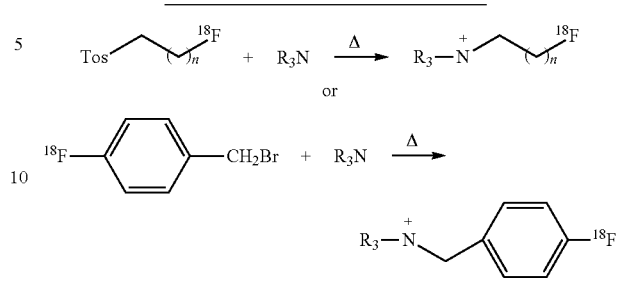

R = phenyl and/or alkyl moieties

Example 8

Whole Body PET/SPECT Imaging

One imaging protocol suitable for delivery of a salt of the invention involves intravenous administration of the salt and acquisition of static scan for several minutes per bed position. The exact scan duration may be varied depending upon patient size, salt dosage, and the nature of the tissue to be imaged. However imaging parameters for imaging primates, particularly humans, can be modified as necessary by one skilled in the radiological arts and familiar with PET and/or SPECT imaging with other radiopharmaceutical agents.

Example 9

Radiolabeling of F-18-FBnTP and Stability in Plasma After Injection of the Agent into Mice Radiochemical purity of F-18-FBnTP and its stability in vivo was measured by chromatography.
Methods:
Preparation of F-18-fluorobenzyl triphenyl phosphonium (F-18-FBnTP): The synthesis of labeling FBnTP with F-18 in the ortho position is described schematically below. After collecting the F-18-fluoride in Kryptofix (as with the fluoroalkyl derivatives), a nitrobenzaldehyde in acetonitrile is added to the mixture. After heating, the aldehyde is reduced to the alcohol and subsequently converted to a radiolabeled benzyl halide. The fluorinated benzyl halide is reacted with triphenylphosphine or its analog in toluene. The mixture is purified and quality control performed, as discussed above Synthesis of o-F-18-fluorobenzyl triphenyl phosphonium ions

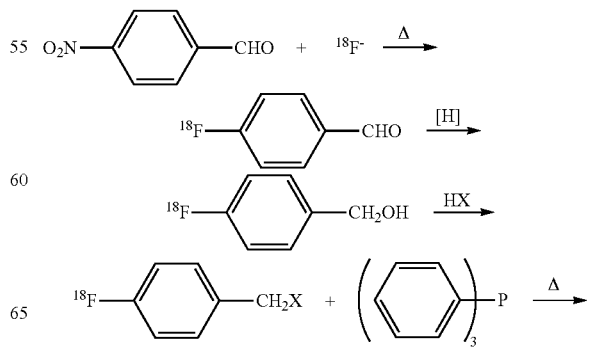

-continued

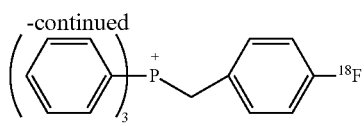

Samples of mouse plasma were obtained from heparinized whole bloodcollected 5, 15 and 30 min p.i. of the tracer. To eliminate binding to plasma proteins, the plasma was added to solid urea to give a final concentration of 8M urea. The plasma-urea was loaded into a column switch HPLC system (Hilton 2000), in which the plasma passes through a small capture column (Oasis Sorbent, Waters Corp.), which retains lipophilic solutes, while polar species fail to bind and are detected as they pass through a positron detector. After four minutes, the capture column is free of plasma proteins and polar species. Then, the contents of the capture column was swept onto an analytical column (Prodigy ODS-3, Phenomenex) by 40% acetonitrile, 60% triethylamine acetate buffer pH 4.1 at 1 mL/min, where separation of the parent compound and lipophilic metabolites occurs. The effluent from the analytical column also passes through the positron flow detector. The proportion of each species is determined from the area under each chromatographic peak. Results: Radiochemical purity of the 18F-labeled FBnTP was more than 95%. Chromatography of plasma revealed a single radio-peak, comprising 97% of total activity with no other peak observed. FIG. 1 depicts the chromatogram of plasma collected 30 min p.i., and the parental compound incubated for a similar time period (30 min) in buffered saline. Plasma activity and parental compound peaked at same time (~6 min).

These radiochromatograms are good evidence of the F-18-FBnTP can be labeled with high radiochemical purity and stable more than 30 min after intravenous injection of the tracer in mice in vivo.

Example 10

Stability of FBnTP Fluorination

Methods: Mice were injected via the tail vein with 25 µCi of F-18-PhC; 5 and 30 min p.i., the left or right femur bone was removed, and bone radioactivity together with standard (1:100 of injected dose) were counted in a gamma counter. A parallel group of mice was injected with free fluorides (F-18). Three mice of each group were studied at each time point. Radioactivity is represented as percentage of injected dosed (% ID) and total bone uptake was calculated as activity in femur bone ×20.

Results: FIG. 2 depicts the total bone uptake at 5 and 30 min p.i. The marginal bone uptake of F-18-PhC, compared to the bone uptake in mice injected with F-18 only, indicates the stability of fluorination of the phosphonium compound. The minimal bone uptake of F-18-FBnTP in bone indicate the lack of free fluorides, meaning the stability of fluorination Example 11

Mitochondria Membrane Potential (MMP)-Dependent Uptake

The extent of MMP-dependent cellular uptake of F-18-FBnTP was assessed using CCCP, a known protonophore that selectively abolishes the MMP.

Methods: Human lung carcinoma H549 cells (10/ml) were incubated with 0.1 µCi/ml F-18-FBnTP for 30 min. Samples of the suspension (1 mL) were transferred to Eppendorf's vials and placed in a 370 C bath. Varying concentrations (30, 60, 90, 120 µM) of CCCP were added to the suspension. After 30 min of incubation with CCCP, the Eppendorf vials were centrifuged for 1 min, and activity in pellet and supernatant was immediately counted.

Results: FIG. 3 depicts the cellular uptake of F-18-FBnTP in the presence of varying concentrations of CCCP. CCCP induced a dose-dependent decrease of the F-18-FBnTP cellular uptake. The large majority (86%) of F-18-FBnTP cellular uptake is MMP-dependent.

Example 12

Biodistribution of Novel F-18-fluorophosphoinium Cations Comparison with Various Tracers Methods: The biodistribution of novel phosphonium compounds F-18-fluorbenzyl triphenyl phosphonium (FBnTP) and F-18-fluopropyl triphenyl phosphonium cation (FPTP) was studies in adult mice and compared with the tracers C-11-triphenylmethyl phosphonium (TPMP), tetraphenyl phosphonium (TPP) and Tc-99m-sestamibii (MIBI). F-18-FBnTP was prepared as describe above. Preparation of FPTP is described below. TPMP was prepared as previously described (Madar I, J Nucl Med. 1999; 40:1180-5). TPP and MIBI were purchased from (NEN and Dupont, respectively). Three to five mice were used for the biodistribution study of each tracer. Nonanesthetized animals were injected i.v. with tracer solution (FBnTP or FPTP, TPMP 25 µCi; MIBI 40 µCi; TPP 2 µCi, all in a volume of 0.2 mL saline) then killed by neck dislocation at 60 min after injection. The organs and tissues of interest were removed and counted by a radioactivity counter along with standards (1:1000) (LKB Wallac, 1282 Compugamma CS).

Preparation of F-18-fluoropropyl triphenyl phosphonium ion (FPTP)

Schematic drawing of F-18-FPTP synthesis is given below. F-18-FPTP was first prepared as the nonradioactive compound, fluoropropyltriphenyl phosphonium bromide, from 1-fluoro-3-bromopropane and triphenylphosphine. The cold compound was characterized by proton and carbon-13 NMR, as well as HPLC. This standard was used for comparison during the purification, quality control and determination of specific activity of the radiolabeled F-18-FPTP. The F-18-FPTP was synthesized as described in FIG. 3. Briefly, 1,3-ditosylpropane in acetonitrile was added to a dried vial containing F-18-fluoride, Kryptofix and potassium carbonate. After heating at 80° C. for 4 minutes on a heat gun, triphenylphosphine in toluene was added to the vial. After 5 minutes, the volume of the solution decreased to a few microliters. After cooling to room temperature, HPLC solvent was added to the vial. The mixture was filtered through a 0.45 micron filter and injected onto a semi-preparative HPLC column. The product, F-18-FPTP, was collected, the solvent evaporated and the remaining dry F-18-FPTP redissolved in sterile normal saline. The solution was filtered through a sterile 0.22 micron filter into a sterile evacuated vial. An aliquot was removed to determine chemical and radiochemical purity by analytical HPLC. The specific activity was also determined at this time.

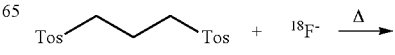

-continued

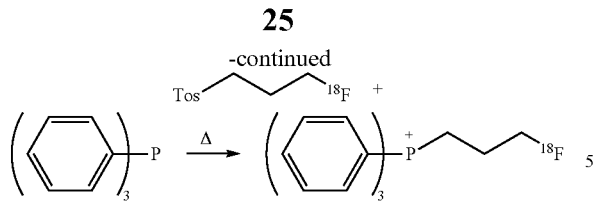

Synthesis of F-18-fluoropropyltriphenyl phosphonium ion

Results: The biodistribution of the tracers is presented in Table 1. Our comparative biodistribution studies in mice indicate that F-18-FBnTP act even better than C-11-TPMP as a PET perfusion agent. F-18-FBNTP uptake in heart is significantly greater than the other tracers, even that of C-11-TPMP, whereas clearance from blood is as good as that of the C-11-TPMP. Many investigators have reported that apoptosis plays a significant role in acute myocardial infarction and the pathogenesis of other forms of heart failure. These data suggest that F-18-FBnTP has a potential utility to assess myocardial diseases including apoptosis in connection with the MMP function as well as the myocardial perfusion tracer.

TABLE 1

Biodistribution of fluorophosphonium cations in mice 60 min after iv. injection in comparing with various tracers.

|  | [18F]FBnTP | [18F]FPTP | [11C]TPMP | [$^3$H]TPP | [$^{99m}$Tc]MIBI |
|---|---|---|---|---|---|
| blood | 0.02 ± 0.00 | 0.01 ± 0.00 | 0.03 ± 0.00 | 0.09 ± 0.02 | 0.26 ± 0.05 |
| brain | 0.07 ± 0.01 | 0.03 ± 0.00 | 0.06 ± 0.02 | 0.06 0.02 | 0.08 ± 0.04 |
| heart | 35.39 ± 5.02 | 9.86 ± 0.82 | 13.4 ± 0.95 | 20.7 ± 1.92 | 5.08 ± 0.25 |
| lung | 7.38 ± 1.55 | 2.02 ± 0.34 | 2.20 ± 0.21 | 2.81 ± 0.41 | 0.98 ± 0.19 |
| liver | 3.00 ± 1.12 | 4.22 ± 1.79 | 5.68 ± 0.60 | 6.12 ± 1.08 | 5.55 ± 1.08 |
| spleen | 1.79 ± 0.57 | 1.23 ± 0.26 | 1.43 ± 0.18 | 1.93 ± 0.47 | 1.27 ± 0.33 |
| kidney | 4.89 ± 0.88 | 5.74 ± 0.54 | 3.79 ± 0.83 | 4.37 ± 0.66 | 12.6 ± 2.57 |
| muscle | 4.31 ± 1.30 | 2.06 ± 0.53 | 2.49 ± 0.35 | 2.22 ± 0.41 | 1.56 ± 0.31 |

* = % ID/g

Example 13

Differentiation of Tumor From Inflammation Using F-18-Phosphonim Cations

The carcinogen nitrosomethyl urea (NMU) induces carcinoma tumors solely in the mammary gland of female rats. Therefore, the orthotopic NMU mammary tumor is an excellent model for evaluating tracer tumor selectivity by contrasting radioactivity accumulating in mammary gland infested with carcinoma cells and healthy mammary gland. Freund Complete Adjuvant (FCA) is a well_studied inflammation agent in rats Induction of FCA inflammation in NMU-bearing rats allows for direct quantitation of tracer capability to differentiate carcinoma from inflammation.

Methods:
0.1 ml of nitrosomethyl urea (NUM) was introduced i.p in female rats (150 g). When tumor reached an approximate size of 1 to 1.5 cm, FCA was injected (0.15 ml) to the hind limb footpad. Uptake assays were carried out 3 days thereafter. F-18-FBnTP (0.25 mCi) was injected via tail vein. Sixty minutes later tumor, inflamed tissue and healthy muscle tissue of the opposite limb (control) were collected on ice, weighed and counted in a gamma counter together with standards.

Results: FIG. 3 depicts F-18-FBnTP activity in malignant mammary gland (Tumor), healthy mammary gland (Control gland), inflammation site (Inflammation), normalized to muscle. F-18-FBnTP uptake in tumor is 4-times greater than that in healthy gland, and 3-times greater than in inflammation. F-18-FBnTP differential uptake in mammary gland carcinoma versus healthy gland and inflammation muscle is a good evidence for the efficacy of the invention.

The accumulation of the novel F-18-phosphonium cations, F-18-FBnTP and F-18-fluoropropyl triphenyl phosphonium (F-18-FPTP) in comparison with F18-FDG in FCA-induced inflammation and healthy tissue is presented in Table 2. Induction of inflammation and activity counting were carried out as described above.

Fluorophosphonium compounds accumulate in inflammation much less than FDG (Table 2). These date provide strong evidence to our claim that F-18-phosphonium compound are suitable for differentiation of tumor from inflammation and may resolve a major drawback of F-18-FDG.

Table 2: Accumulation of Fluorophosphonium Compounds (FBnTP and FPTP)

FDG in inflammation tissue and healthy muscle 3 days after administration of FCA.

TABLE 2

Accumulation of fluorophosphonium compounds (FBnTP and FPTP) FDG in inflammation tissue and healthy muscle 3 days after administration of FCA. and

|  | Blood | Inflammation | Control | Inf/Control |
|---|---|---|---|---|
| [$^{18}$F]FPTP | *0.037 ± 0.01 | 0.07 ± 0.01 | 0.29 ± 0.06 | 0.25 ± 0.04 |
| [$^{18}$F]FDG | 0.17 ± 0.06 | 1.20 ± 0.16 | 1.05 ± 0.35 | 1.20 ± 0.29 |
| [$^{18}$F]FBnTP | 0.10 ± 0.01 | 0.27 ± 0.22 | 0.76 ± 0.21 | 0.42 ± 0.40 |
| [$^{18}$F]FDG | 0.40 ± 0.14 | 1.42 ± 0.53 | 0.68 ± 0.14 | 2.12 ± 0.73 |

*= % ID/g tissue

Example 14

Detection of Response of Lung Carcinoma Tumor to the Chemotherapy Agent Taxeter_In Vivo Methods: 2×106 human lung carcinoma A549 cells were inoculated s.q. in 12 nude mice. When tumor size reached an approximate size of 5_10 mm, six mice were injected i.v. with taxeter and six mice served as control. Uptake assays were carried out 48 hours thereafter. 25 µCi of F-18-FBnTP were injected i.v., and tumor and muscle tissue was dissected after 60 min.

Results: FIG. 5 depicts tumor activity normalized to muscle. Taxeter produced a nearly 50% decrease in F-18-FBnTP accumulation in tumor, compared to non-treated mice.

Example 15

Detection of Apoptosis Induced by Androgen Depletion

Methods: Male rats were castrated and uptake assays were conducted 4 days thereafter. The ventral (VP), anterior (AP) and the dorsolateral (DLP) lobes of the prostate were dissected together with hind limb muscle. After counting tracer activity in the tissue samples, TUNEL staining was carried out and the fractions of apoptotic cells in the ventral and anterior lobes were measured.

Figure 8:
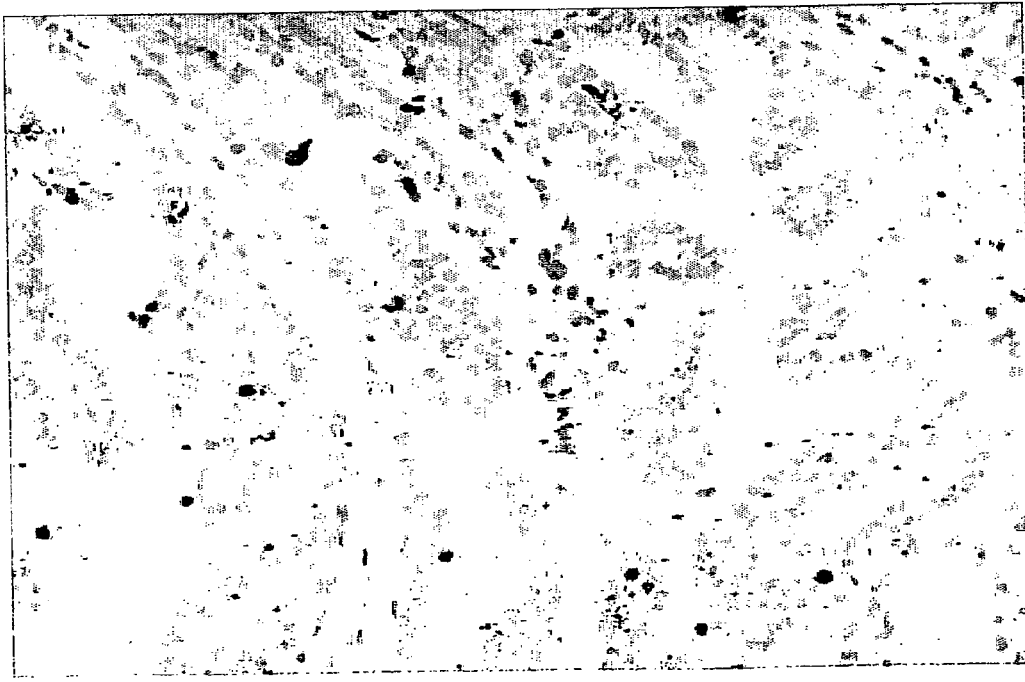

Results: Data in FIG. 6 are the mean of 9 treated and 8 control rats, normalized to muscle. Castration induced a lobe-specific decrease in the ventral aspects, but not in the anterior and the dorsolateral lobes. These finding are in line with fraction of apoptotic cells, as counted in the stained histological section. In the VP lobe, 12.4%±3.8% of cells demonstrated DNA laddering (FIG. 8), compared to only 3.3%±1.7% of cells in the AP lobe (FIG. 9).

Example 16

F-18-FBnTP Selectivity for Prostate Carcinoma

The data presented above show that F-18-PhC is capable of detecting the apoptotic process it the whole animal. In the prostate, moreover, alterations in F-18-PhC accumulation correlate with extent of apoptosis in the target tissue. These data suggest suitability of F-18-PhC as a PET tracer for measuring the efficacy of chemotherapy in prostate carcinoma and most probably in other type of carcinomas as well. However, the capability of a tracer to accurately report of extent of apoptosis may depends on the selectivity of the tracer to the tumor. To address this question, tumor selectivity of F-18-FBnTP was studied in orthotopic model of prostate carcinoma.

Methods: 2×106 cells were injected, under anesthesia, into the prostate epithelial tissue of nude mice. When tumor reached an approximate size of 5 mm, uptake assays were performed as described above. Tumor selectivity of F-18-FBnTP and F-18-FDG was compared (3 mice in each group)

Results: FIG. 9 depicts the accumulation of tracer in the normal and malignant prostate, normalized to muscle. The uptake ratio of malignant-to-normal prostate tissue was 2.5 for F-18-PhC and 1.25 for FDG. This data provides further support for the suitability of F-18-PhC to detect prostate carcinoma and to measure response to treatment.

Example 17

C-11-TPMP Uptake Kinetics in the Myocardium

We have examined the performance of C-11-triphenyl phosphonium cation (TPMP) for assessing regional myocardial flow in dog using PET (Kraus, 1994).

Methods: Four mCi of C-11-TPMP were introduced i.v., and dynamic images of increasing duration (15 sec to 20 min) were acquired over a total time of 85 min. Images were acquired on the GE 4096+ PET scanner (15 slices, 6.5 mm slice thickness). Images were reconstructed using back-projection, and corrected for attenuation. A detailed description of methods appears in Kraus, 1994.

Results: Axial sections of the heart at 5, 30 and 60 min after injection are shown in FIG. 10. These images show excellent visualization of the myocardium with a high contrast to the surrounding lung tissue. During the plateau time period heart/lung ratio was >14:1, and heart/blood >100:1.

The extraction fraction of C-121-TPMP in the dog heart as a function of myocardial blood flow is shown in FIG. 11. Under baseline conditions (flow=69 ml/min/100 g), the extraction fraction is very high (91%). A five-fold increase (by adenosine) in flow resulted in a 39% decrease of the extraction fraction.

To investigate the relationship between myocardial blood flow and C-11-TPMP uptake in the heart, the LAD was occluded and the C-11-TPMP accumulation in tissue samples compared to microsphere determined regional myocardial blood flow. A significant correlation (r=0.93, p<0.01) was found at 5 min after LAD occlusion (FIG. 12). The non-infracted/infracted myocardium ratio was 12.1±2.4.

These data point out the excellent features of the phosphonium cation as a perfusion agent for assessing myocardial blood flow, compared to other currently used SPECT perfusion agents. Thallium 201 extraction under baseline flow is about 80%, decreasing to about 60% for five-fold increases in flow rate. MIBI extraction for a normal flow is about 60%, decreasing to 40% for high flow rates. The advantages of C-11-TPMP PET technology over these SPECT agents are: (1) an overall higher myocardial extraction of C-11-TPMP; (2) a prolonged retention of C-11-TPMP in the myocardium; and (3) the better temporal and spatial resolution of the PET scanner for better documentation of ischemic regions in the myocardium.

Example 18

F-18-FBnTP Uptake Kinetics in the Myocardium

Methods: Mongrel dogs (BW=35 kg) were injected with 3-4 mCi of F-18-FBnTP. Images were acquired on a GE 4096+ scanner (15 slices, 6.5 mm slice thickness). PET scans of increasing duration (15 sec to 20 min) were acquired over a total time of 85 min post-injection. Arterial blood samples (0.5 ml in volume) were collected every few seconds for the first 3 minutes and at gradually increasing intervals (1 to 10 min) for the remaining time of the imaging study. The vascular and myocardial kinetics of F-18-FBnTP was analyzed using the ROI method.

Results: F-18-FBnTP demonstrated a rapid washout from the blood pool (FIG. 13). F-18-FBnTP accumulated rapidly in the myocardium, reached equilibrium within a few minutes which persisted for the remaining scanning time (FIG. 14). Rapid uptake was seen in both the left and right ventricle (FIG. 15). In contrast, F-18-FBnTP demonstrated rapid clearance from the atrium as well as from the adjacent lungs (FIG. 15). At 60-85 min post-injection period the ratio of myocardium to atrium and to lung was >15:1. Consequently, F-18-FBnTP afforded high-contrast cardiac images of an excellent visual clarity (FIG. 16).

Example 19

F-18-FBnTP Myocardial Accumulation in Heart Failure

Pacing of the mongrel dog heart at high rate (210 bpm) for a four weeks is a well-established model of heart failure. The advantage of this model is that the cardiomyopathy solely involve apoptosis without stenosis of coronary artery or related ischemia. Therefore, in this model the affect of apoptosis on FBnTP uptake can be dissected.

Methods: Preparation of dog and data acquisition was performed as described above. Mongrel dog was installed with a pacemaker in the rib case and underwent FBnTP PET scan (presented above). Following the baseline scan, the dog_s heart was paced at a rate of 210 bpm for 4 weeks and a second scan was acquired.

Results: FIG. 17 depicts the short-axis images of FBnTP before and after 4-wks pacing. Pacing produced a significant decease in FBnTP uptake of 40-60% throughout most of the inferior wall (FIGS. 18-19, Table 3). Despite that the PET scan was not gated, but due to the superb perfusion capacities of FBnTP and consequently excellent clarity of the myocardium left ventricular wall, pacing-induced remodeling of the myocardium typical to heart failure, including thinning of the left ventricular wall and dilation of the left ventricular chamber can be seen clearly.

Moreover, pacing induced a significant decrease in the accumulation of F-18-FBnTP throughout the entire inferior wall, indicating an enhanced process of heart failure mediating apoptosis of myocytes in this segment. FIG. 18 depicts co-registered images before and after pacing. A significant decrease in F-18FBnTP uptake is seen in the inferior wall.

Quantitation of FBnTP in the myocardium was performed using region of interest placed on co-registered myocardial images, whose activity was normalized to the injected dose, before and after pacing. An example for ROI placement is illustrated in FIG. 18.

Myocardial pacing induced a significant (p<0.001) decrease of 40 to 60% in the inferior wall (see table 3)

TABLE 3

F-18-FBnTP myocardial uptake before and after pacing. For positioning of ROI see FIG. 18. Data were derived as illustrated in FIG. 19

|  | Baseline | 4-Wks Pacing | Ratio P/B |
|---|---|---|---|
| Slices 46-49 | | | |
| ROI1 | *108.62 | 60.70 | 0.56 |
| ROI2 | 118.89 | 90.93 | 0.76 |
| ROI3 | 119.11 | 97.86 | 0.82 |
| Slices 36-37 | | | |
| ROI1 | 72.22 | 44.46 | 0.62 |
| ROI2 | 89.40 | 81.06 | 0.91 |
| ROI3 | 102.46 | 86.93 | 0.85 |

*average activity (% of injected dose) accumulated over the over 36 to 85 min per slice, mean of activity of denoted coronal slices. Position of ROIs as depicted in the above upper left image. Same ROIs template was used to retrieve all data.

The disclosures of all articles and references mentioned in this application, including patents, are incorporated herein by reference.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A method of imaging cardiac infarction, cardiac perfusion, heart failure, cardiomyopathy or ischemia comprising:
   providing a radiolabeled salt comprising at least one pharmaceutically acceptable anion and $^{18}$F-4-fluorobenzyl-triphenylphosphonium ion;
   contacting cells or tissues in a subject with the radiolabeled salt; and
   making a radiographic image.

2. The method of claim 1, wherein the image correlates with mitochondrial membrane potential ($\Delta\Psi m$).

3. The method of claim 2, wherein the image correlates with suppressed or enhanced apoptosis.

4. The method of claim 1, wherein the image correlates with imaging mitochondrial dysfunction.

5. The method of claim 1, wherein the radiolabeled salt exhibits a target to non-target ratio of at least about 5:1.

6. The method of claim 1, wherein the radiolabeled salt is stable in vivo.

7. The method of claim 1, wherein the radiolabeled salt substantially localizes to a site or sites having dysfunctional mitochondria within about 120 minutes after administration.

8. The method of claim 1, wherein the radiolabeled salt substantially localizes to a site or sites dysfunctional mitochondria within about 60 minutes after administration.

9. The method of claim 1, wherein the radiolabeled salt substantially localizes to a site or sites dysfunctional mitochondria within about 30 minutes after administration.

10. The method of claim 1, wherein the radiolabeled salt is detected by a gamma camera, positron emission tomography (PET) or single photon emission tomography (SPECT).

11. The method of claim 1, wherein the subject is a human, rat, mouse, cat, dog, horse, sheep, cow, monkey, avian, or amphibian.

12. The method of claim 1, wherein the cell is a myocyte.

13. The method of any one of claims 7-9, wherein the site or sites are in the myocardium.

* * * * *

UNITED STATES PATENT AND TRADEMARK OFFICE
CERTIFICATE OF CORRECTION

PATENT NO. : 8,524,193 B2
APPLICATION NO. : 10/503690
DATED : September 3, 2013
INVENTOR(S) : Igal Madar et al.

Page 1 of 1

It is certified that error appears in the above-identified patent and that said Letters Patent is hereby corrected as shown below:

In the Specification

Column 1, please replace the second paragraph as follows:
STATEMENT OF GOVERNMENTAL INTEREST
This invention was made with government support under grant number CA092871, AA011872, DA011774, DA012274, awarded by the National Institutes of Health. The government has certain rights in the invention.

Signed and Sealed this
Twenty-fourth Day of April, 2018

Andrei Iancu
*Director of the United States Patent and Trademark Office*